(12) United States Patent
Mitchison

(10) Patent No.: US 6,541,203 B2
(45) Date of Patent: Apr. 1, 2003

(54) DETECTING STRUCTURAL OR SYNTHETIC INFORMATION ABOUT CHEMICAL COMPOUNDS

(75) Inventor: Timothy J. Mitchison, Brookline, MA (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 09/448,395

(22) Filed: Nov. 23, 1999

(65) Prior Publication Data

US 2002/0006614 A1 Jan. 17, 2002

Related U.S. Application Data

(60) Provisional application No. 60/109,725, filed on Nov. 23, 1998.

(51) Int. Cl.[7] .......................... C12Q 1/68; C07H 21/04; C07A 21/02; G01N 33/53; G01N 33/543

(52) U.S. Cl. .......................... 435/6; 435/7.5; 536/23.1; 536/24.3; 536/24.33; 436/518

(58) Field of Search ............................ 536/23.1, 24.3, 536/24.33, 22.1; 435/6, 7.5, 810; 436/518, 536

(56) References Cited

U.S. PATENT DOCUMENTS

| | | | | |
|---|---|---|---|---|
| 5,412,087 A | * | 5/1995 | McGall et al. | 536/24.3 |
| 5,723,598 A | | 3/1998 | Lerner et al. | 536/25.3 |
| 6,027,890 A | * | 2/2000 | Ness et al. | 435/6 |

FOREIGN PATENT DOCUMENTS

| | | | |
|---|---|---|---|
| WO | WO 93/06121 | * | 4/1993 |
| WO | WO 95/12608 | | 5/1995 |
| WO | WO 95/28640 | | 10/1995 |
| WO | WO 95/29473 | | 11/1995 |
| WO | WO 95/35503 | | 12/1995 |
| WO | WO 97/14814 | | 4/1997 |
| WO | WO 98/25146 | | 6/1998 |

OTHER PUBLICATIONS

Thompson et al. Synthesis and Application of Small Libraries. Chemical Review. vol. 96, pp. 555–600. Dec. 1996.*
Ohlmeyer et al. Complex synthetic chemical libraries indexed with molecular tags. Proc. Natl. Acad. Sci. USA vol. 90, pp. 10922–10926, Dec. 1993.*
Nestler et al. General Method for molecular tagging of encoded combinatorial chemistry libraries. J. Org. Chem. vol. 59, No. 17, pp. 4723–4724. Dec. 1994.*
Schena et al. Quantitative monitoring of gene expression patterns with a complementary DNA microarray. Science vol. 270, pp. 467–470, Oct. 1995.*
Guo et al. Direct Fluorescence analysis of genetic polymorphisms by hybridization with oligonucleotide arrays on glass supports. Nucleic acids research vol. 22, No. 24, pp. 5456–5465, Dec. 1994.*
Ahern, Biochemical, Reagents kits offer scientists good return on investment. The Scientist, vol. 9, No. 15, pp. 1–5, Jul. 1995.*
Ainsworth et al., *Meth. Mol. Biol.* 31:205–210, 1994.
Borman, "Combinatorial Chemistry" *Chem. and Eng. News* 43, Feb. 24, 1997.
Czarnik et al., "Encoding methods for combinatorial chemistry" *Curr. Op. Chem. Biol.* 1:60–66, 1997.
Davis et al., "Use of a high affinity DNA ligand in flow cytometry" *Nucleic Acids Research* 24(4):702–706, 1996.
DeRisi et al., "Exploring the Metabolic and Genetic Control of Gene Expression on a Genomic Scale" *Science* 278:680–686, 1997.
Detter et al., "Identification of novel simple sequence length polymorphisms (SSLPs) in mouse by interspersed repetitive element (IRE)–PCR" *Nucleic Acids Research* 26(17):4091–4092, 1998.
Dreyfuss et al., "Chemistry of Silane Coupling Reactions. 2. Reaction of Dimethylmethoxysilanated Poly(butadiene) with Triethylsilanol and with Glass" *Macromolecules* 11(5):1036–1038, 1978.
Ellington, "Aptamers acheive the desired recognition" *Current Biology* 4(5)427–429, 1994.
Ellington et al., "Selection in vitro of single–stranded DNA molecules that fold into specific ligand–binding structures" *Nature* 355:850–852, Feb. 27, 1992.
Fitzwater et al., "A SELEX Primer" *Methods in Enzymology* 267:275–301, 1996.
Furka et al., "General method for rapid synthesis of multi-component peptide mixtures" *Int. J. Pept. Protein Res.* 37:487–493, 1991.
Hertl, "Mechanism of Gaseous Siloxane Reaction with Silica" *J. Phys. Chem.* 72(4):1248–1253, 1968.
Jacobsen et al., *Curr. Opi. Struct. Biol.* 5(6):818–824, Dec. 1995.

(List continued on next page.)

*Primary Examiner*—Kenneth R. Horlick
*Assistant Examiner*—Cynthia Wilder
(74) *Attorney, Agent, or Firm*—Choate, Hall & Stewart; Brenda Herschbach Jarrell

(57) ABSTRACT

The present invention provides an improved system for the rapid and non-destructive identification of chemical compounds attached to solid supports. In general, the invention provides an identification unit comprising a tag attached to the solid support and a binding partner that interacts specifically and detectably with he tag. In preferred embodiments, the identification unit incorporates the advantages of chemically robust tags and a decoding technique capable of amplification for easy detection and analysis. The present invention further provides a kit comprising a collection of tags capable of attachment to a support and binding partners capable of binding selectively and detectably to the tags, to generate an identification unit for the facile determination of the structure of a compound of interest by determining the reaction history and/or structural characteristics of the compounds that are encoded by the identification unit.

29 Claims, 26 Drawing Sheets

OTHER PUBLICATIONS

Jenison et al., "High–Resolution Molecular Discrimination by RNA" *Science* 263:1425–1429, Mar. 11, 1994.

Klug et al., "All you wanted to know about SELEX" *Molecular Biology Reports* 20:97–107, 1994.

Nestler et al., "General Method for Molecular Tagging of Encoded Combinatorial Chemistry Libraries" *J. Org. Chem.* 59(17):4723–4724, 1994.

Ohlmeyer et al., "Complex synthetic chemical libraries indexed with molecular tags" *Proc. Natl. Acad. Sci. USA* 90:10922–10926, Dec. 1993.

Sarkar et al., "An NMR Method To Identify Nondestructively Chemical Compounds Bound to a Single Solid–Phase–Synthesis Bead for Combinatorial Chemistry Applications" *J. Am. Chem. Soc.* 118:2305–2306, 1996.

Sassanfar et al., "An RNA motif that binds ATP" *Nature* 364:550–553, 1993.

Tan et al., "Stereoselective Synthesis of over Two Million Compounds Having Structural Features Both Reminiscent of Natural Products and Compatible with Miniaturized Cell–Based Assays" *J. Am. Chem. Soc.* 120:8565–8566, 1998.

Tautz., "Hypervariability of simple sequences as a general source for polymorphic DNA markers" *Nucleic Acids Research* 17(16):6463–6471, 1989.

Thompson et al., "Synthesis and Applications of Small Molecule Libraries" *Chem Rev.* 96:555–600, 1996.

Tuerk et al., "Systematic Evolution of Ligands by Exponential Enrichment: RNA Ligands to Bacteroiphage T4 DNA Polymerase" *Science* 249:505–510, 1990.

\* cited by examiner-

FIG. 1
DIG @ 0.1% Load
DIG @ 0.01% Load
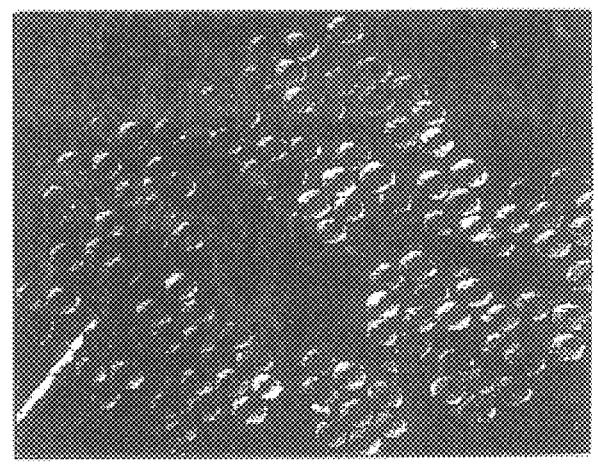
DIG @ 0.001% Load
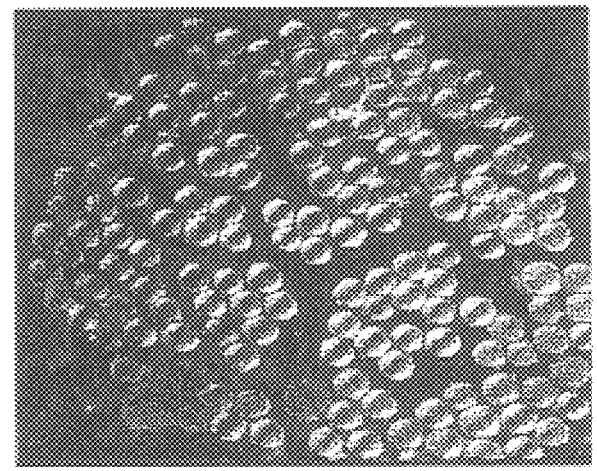

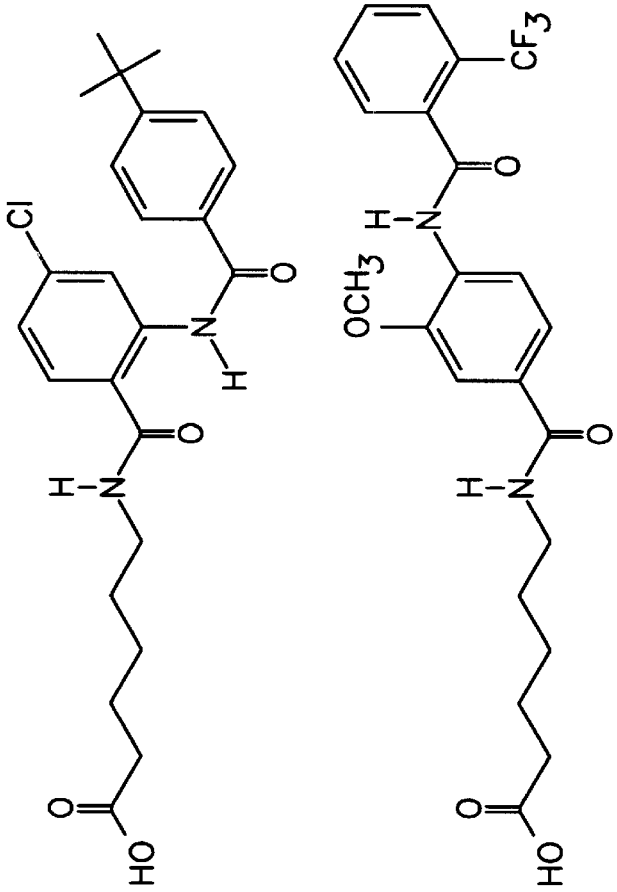
FIG.2-A

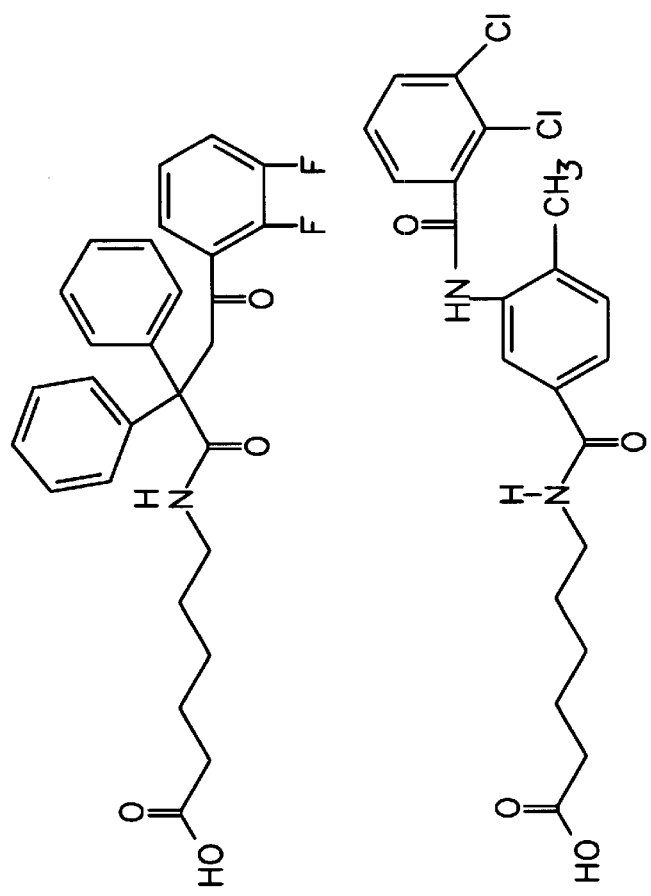
FIG. 2-B

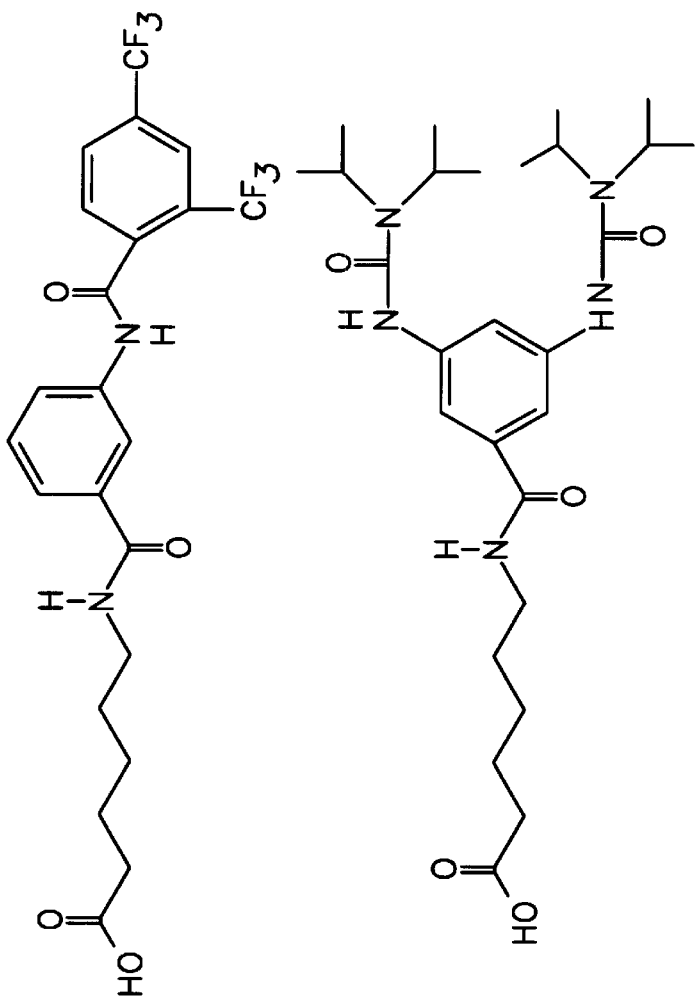
FIG. 2-C

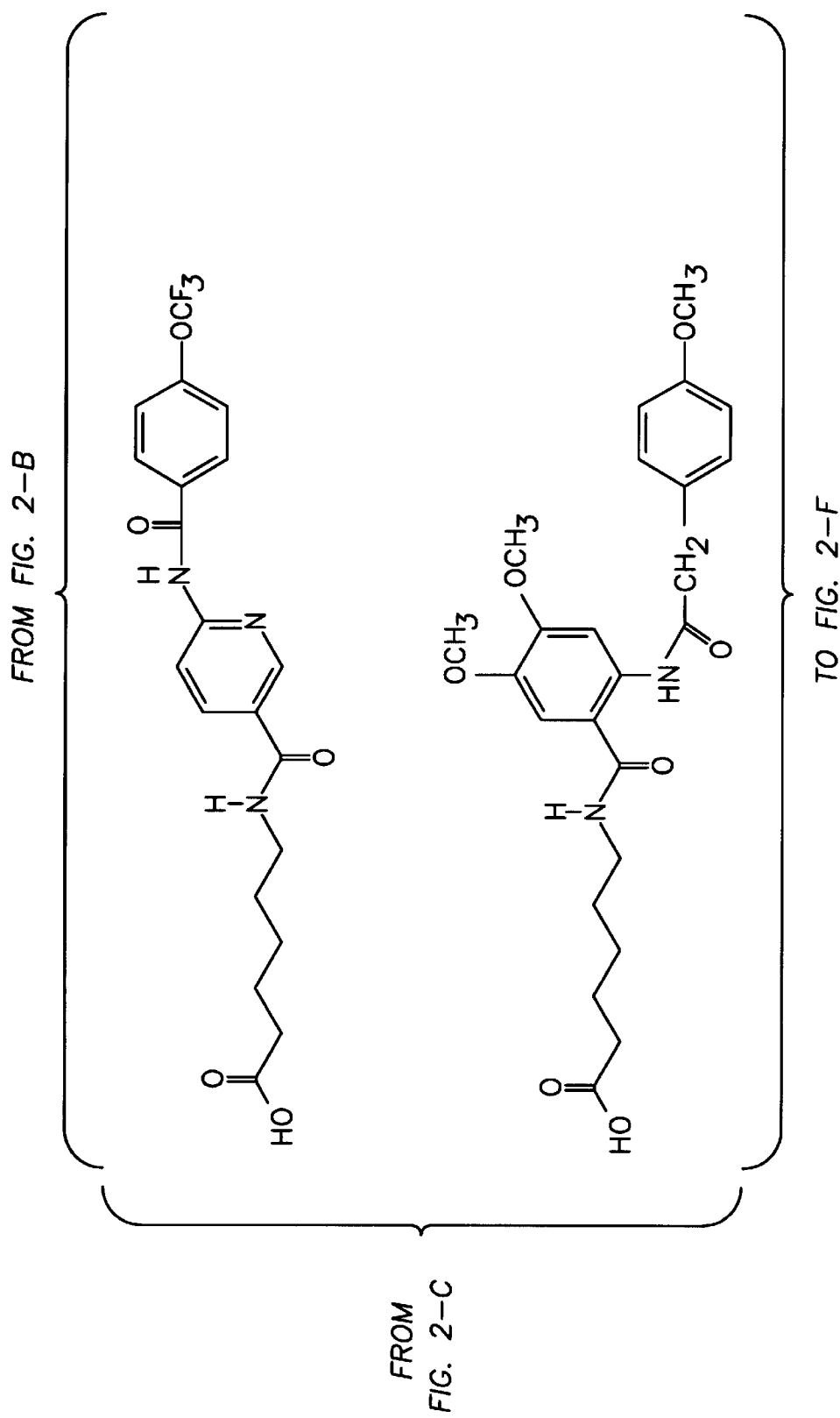
FIG.2-D

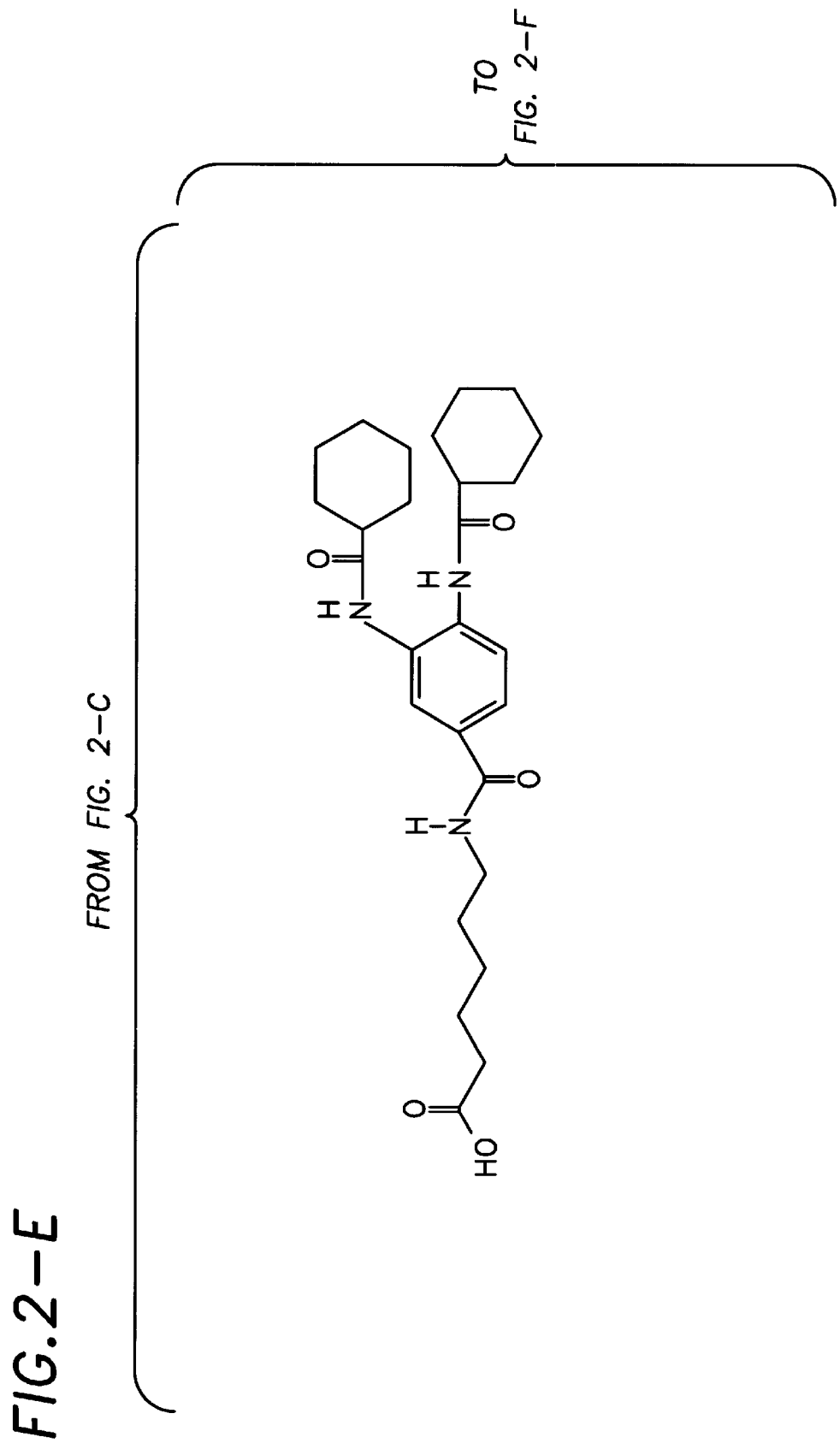
FIG.2-E

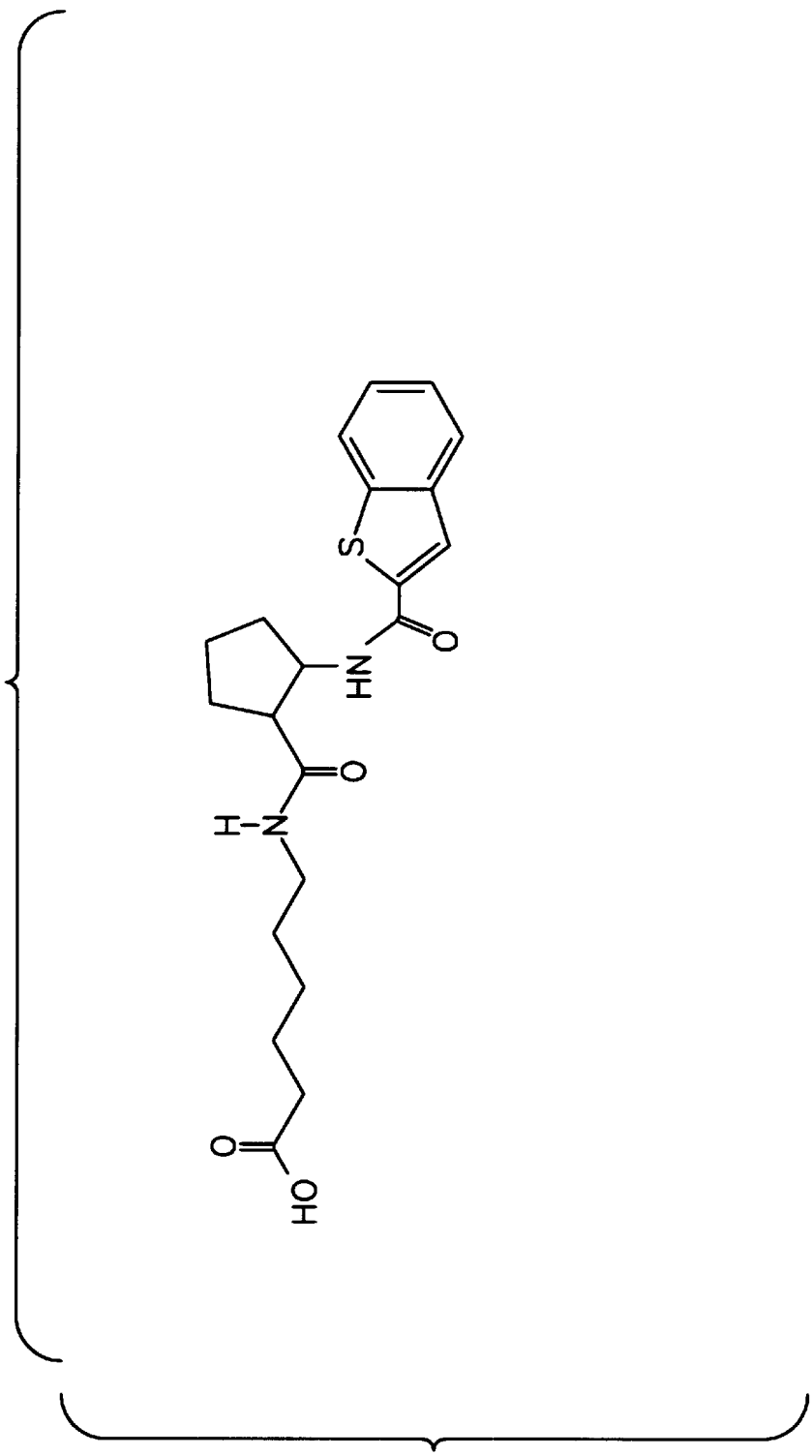
FIG. 2-F

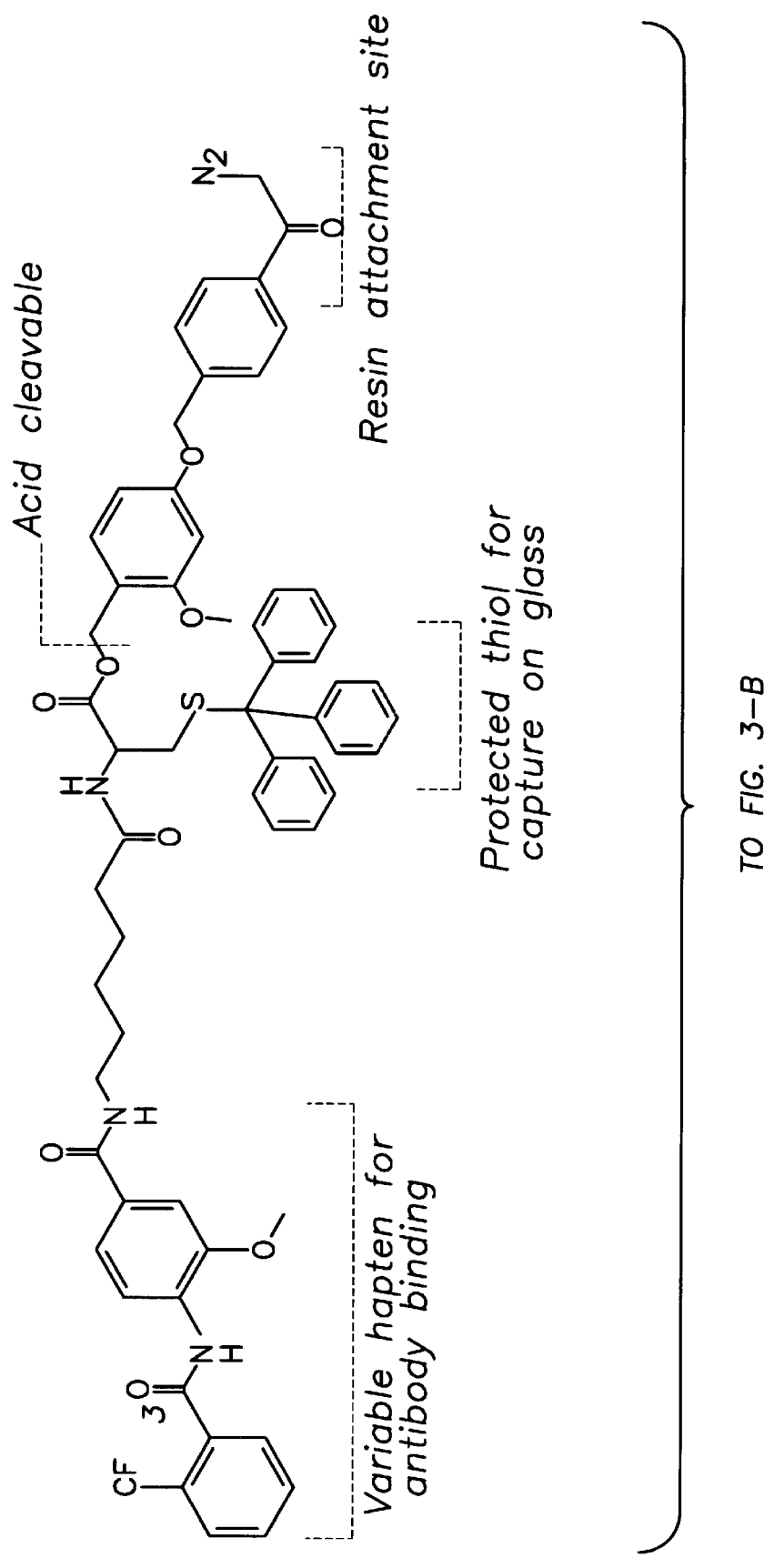
FIG.3-A
TO FIG. 3-B

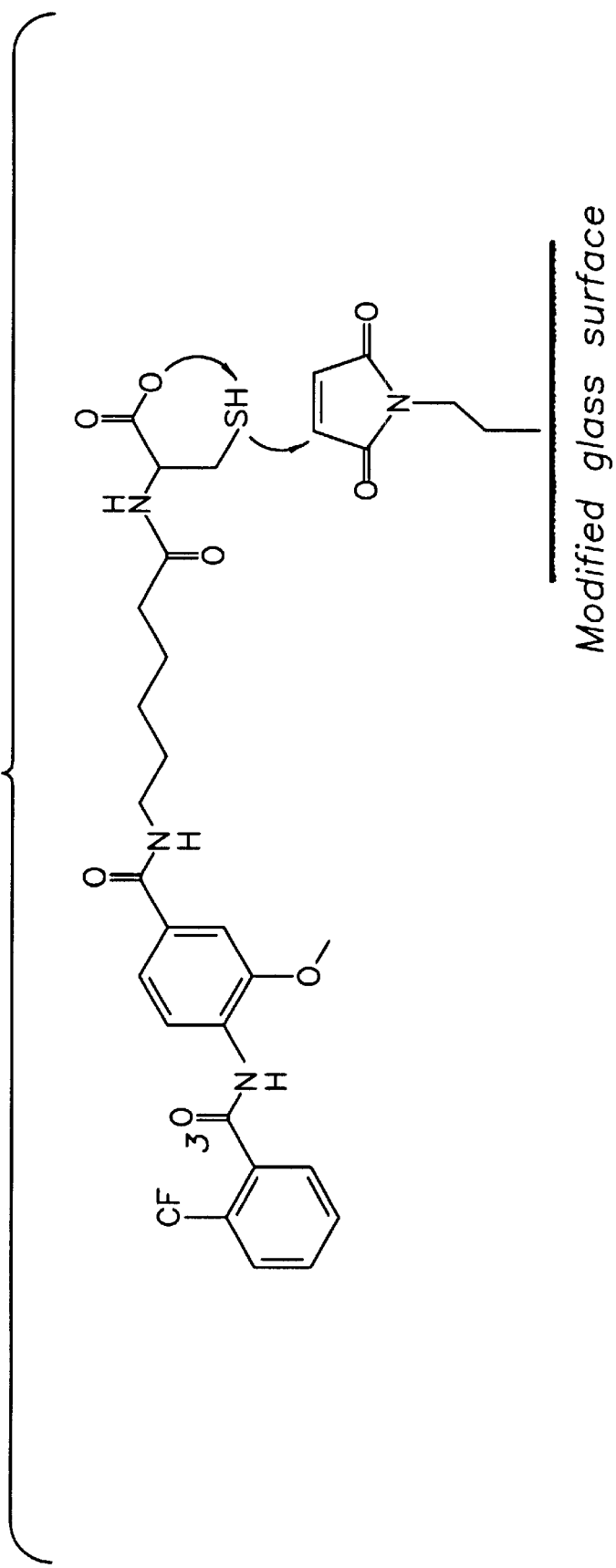
FIG.3-B

HAPTENS
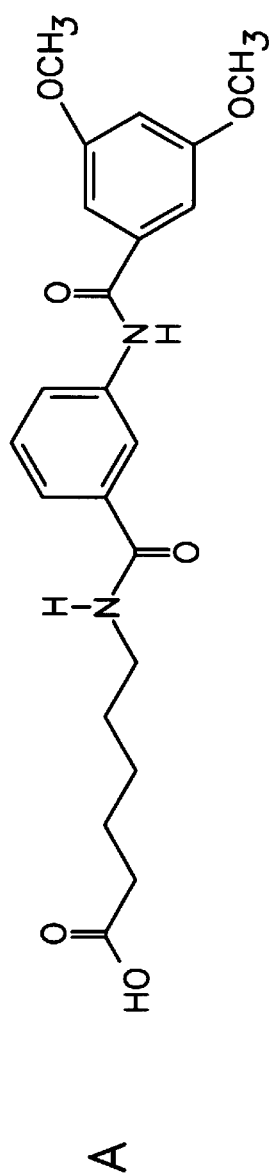
A
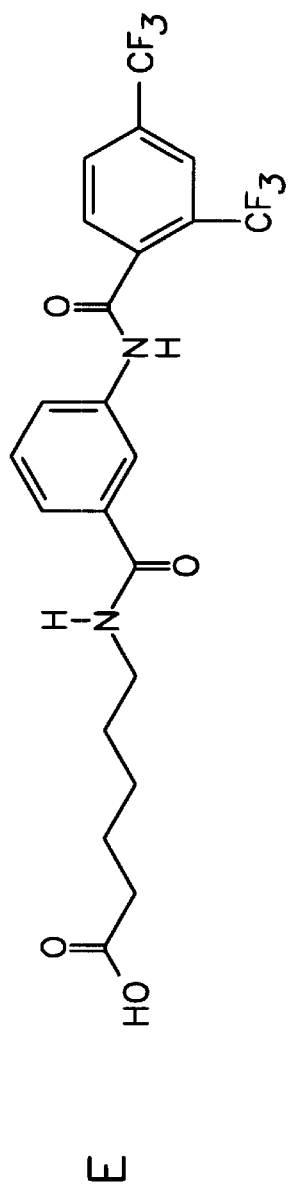
E
FIG.5-A
TO FIG. 5-B
TO FIG. 5-C

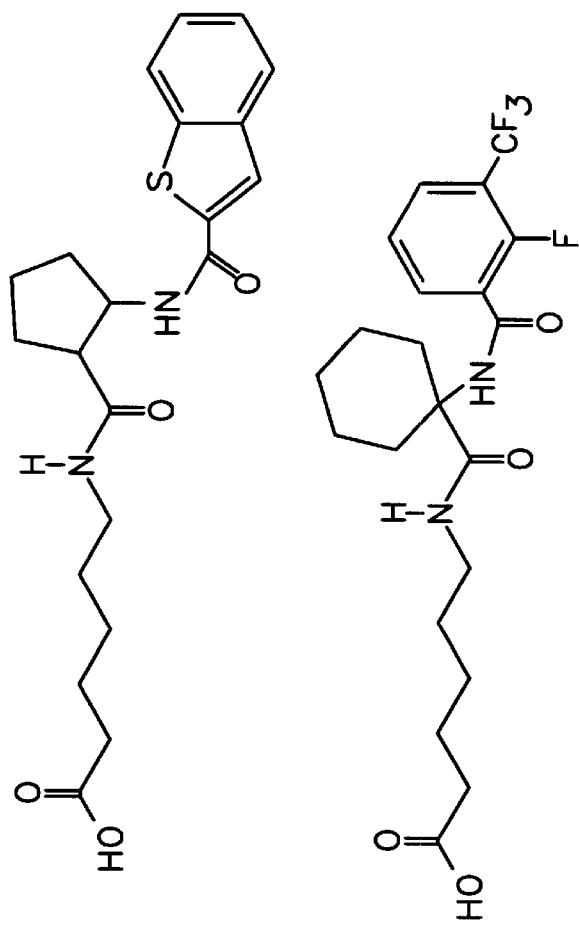
FIG. 5-B

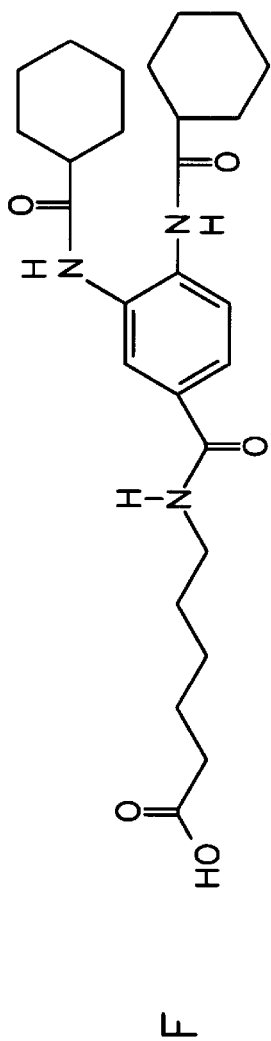
F
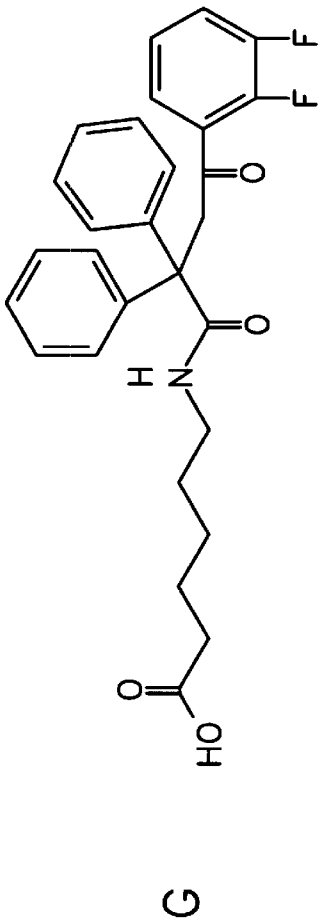
G
FIG. 5-C

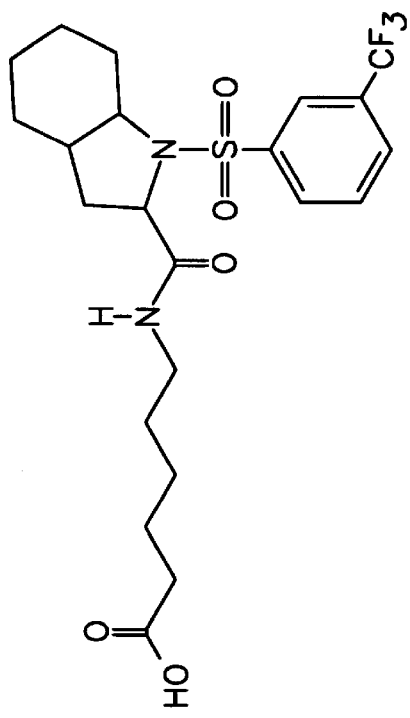
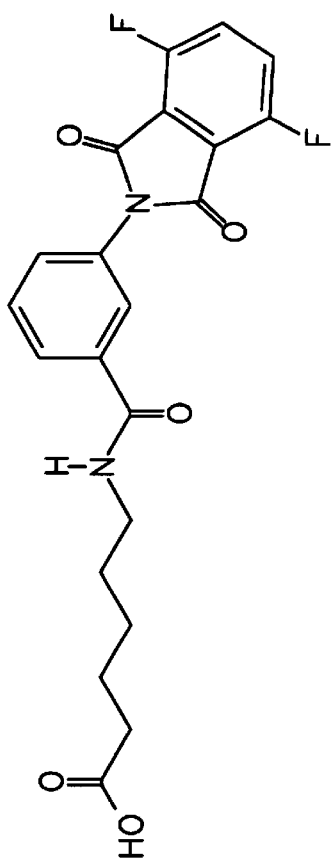
FIG. 5-D

FIG.5-E
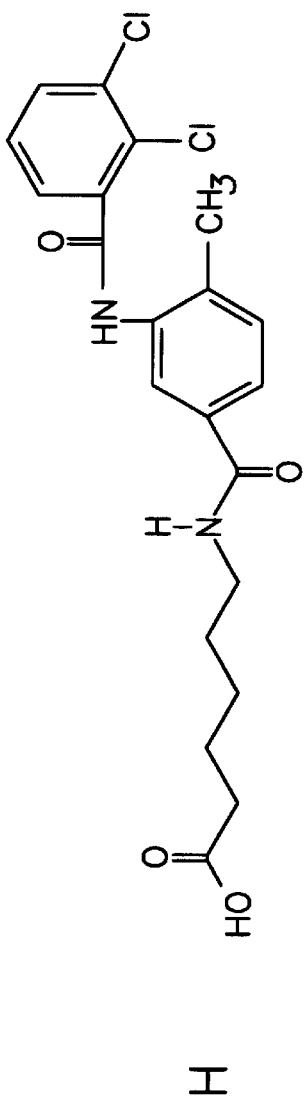
H
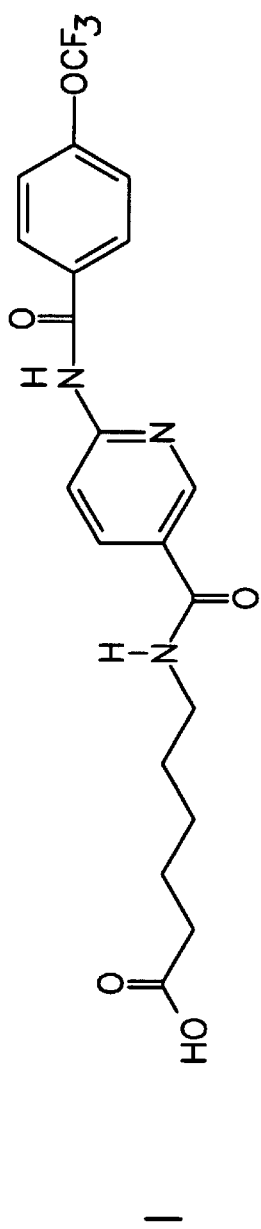
I

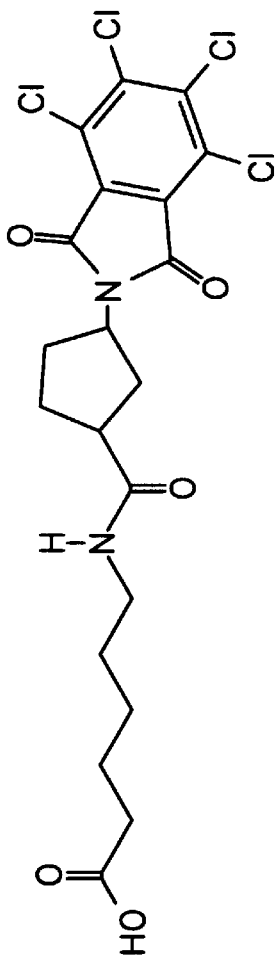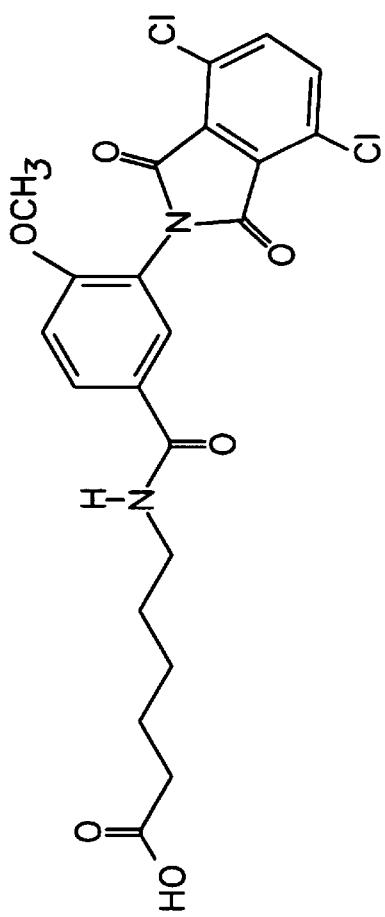
FIG. 5-F

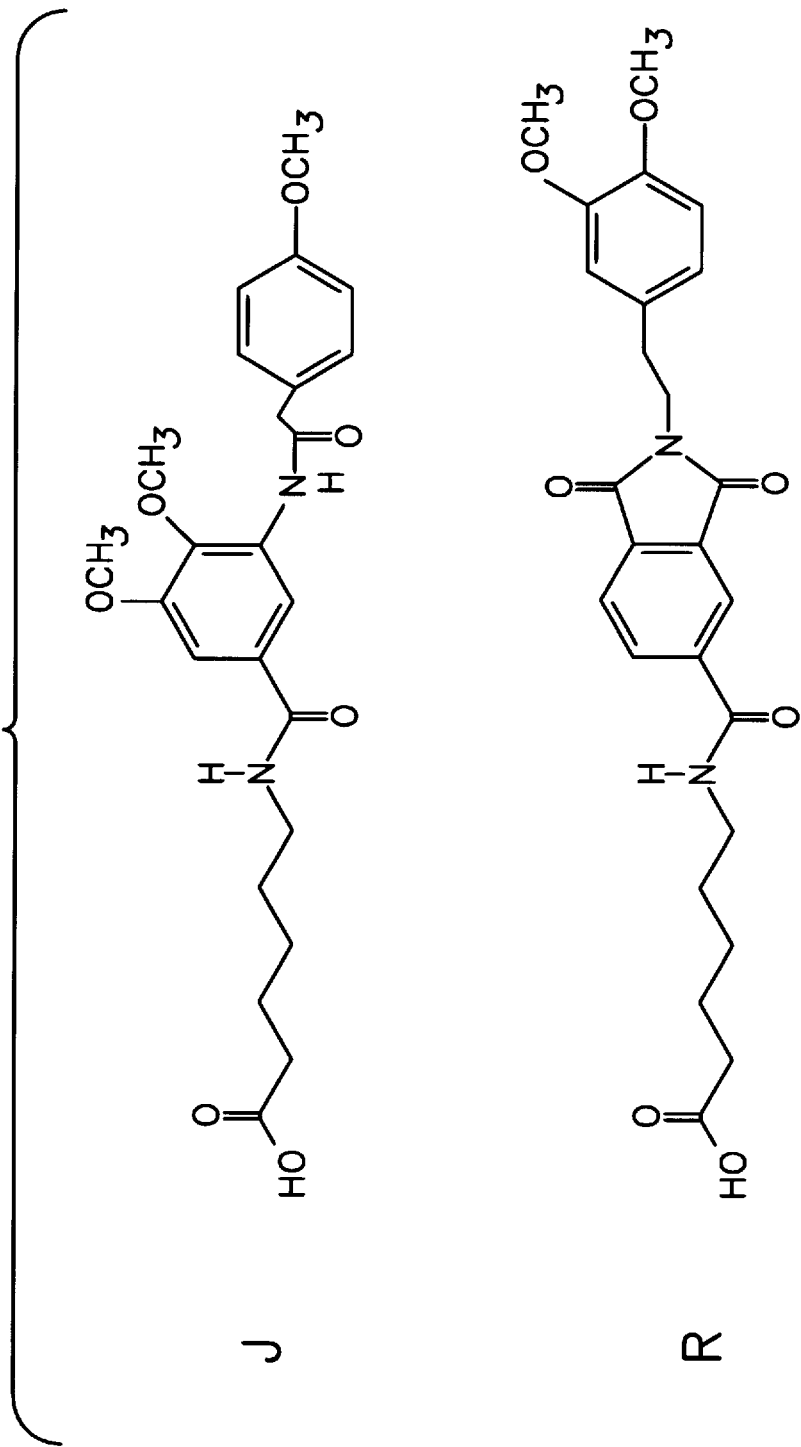
FIG.5-G

FIG.6

| FIG.6-A |  |
|---------|--|
| FIG.6-B | FIG.6-C |

FIG.6-D

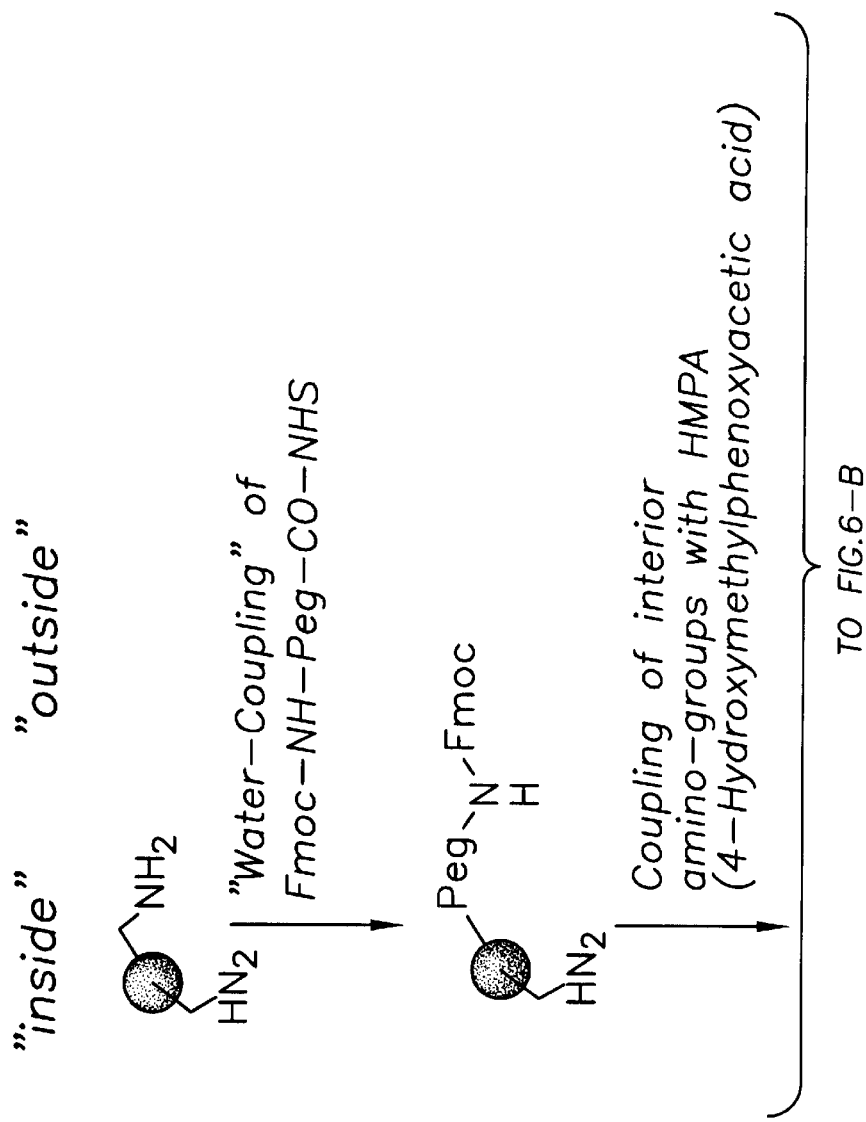
FIG.6-A Synthetic Scheme for Modification of "Inside" and "outside" of Polystyrene Macrobeads with Ligand and Haptens

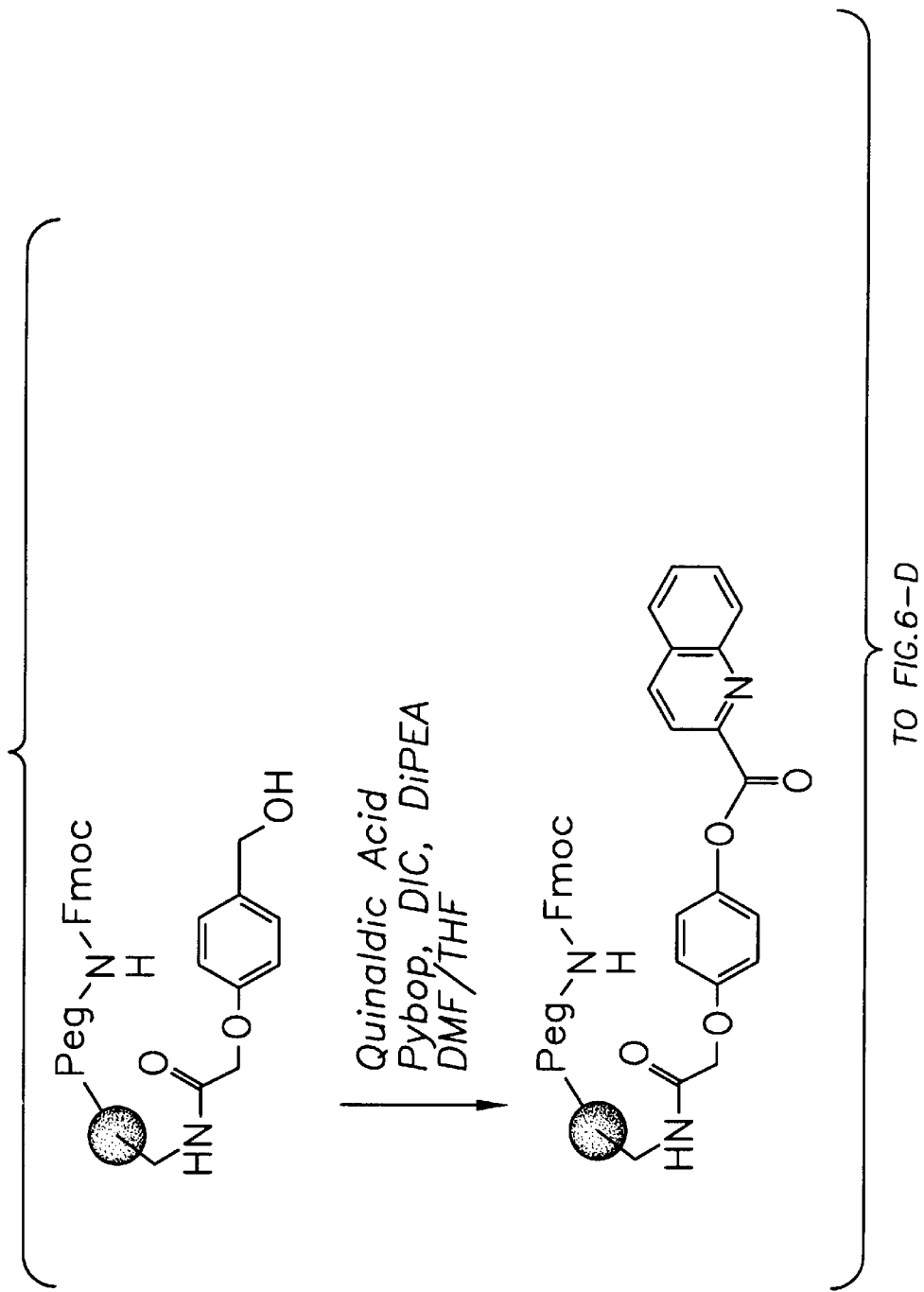
FIG.6-B

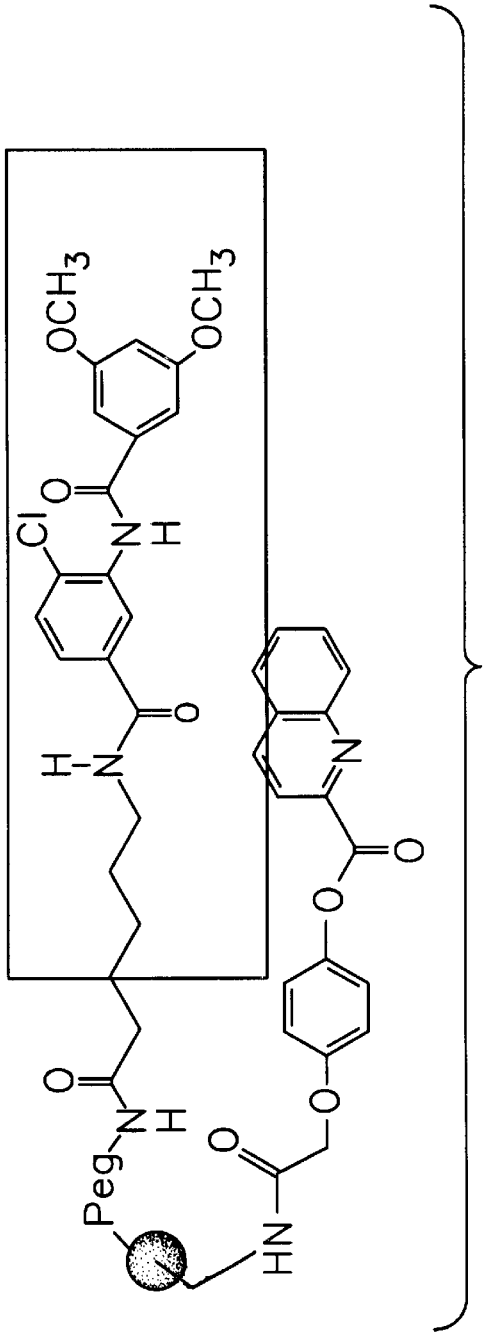
FIG. 6-C

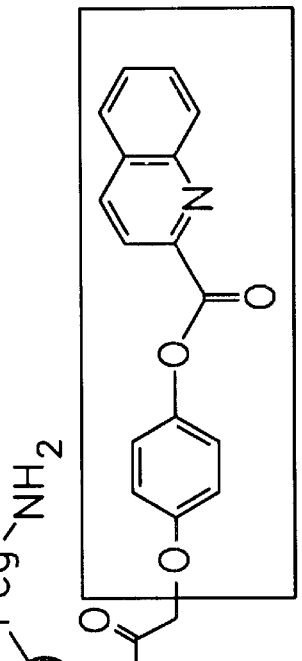
FIG.6-D

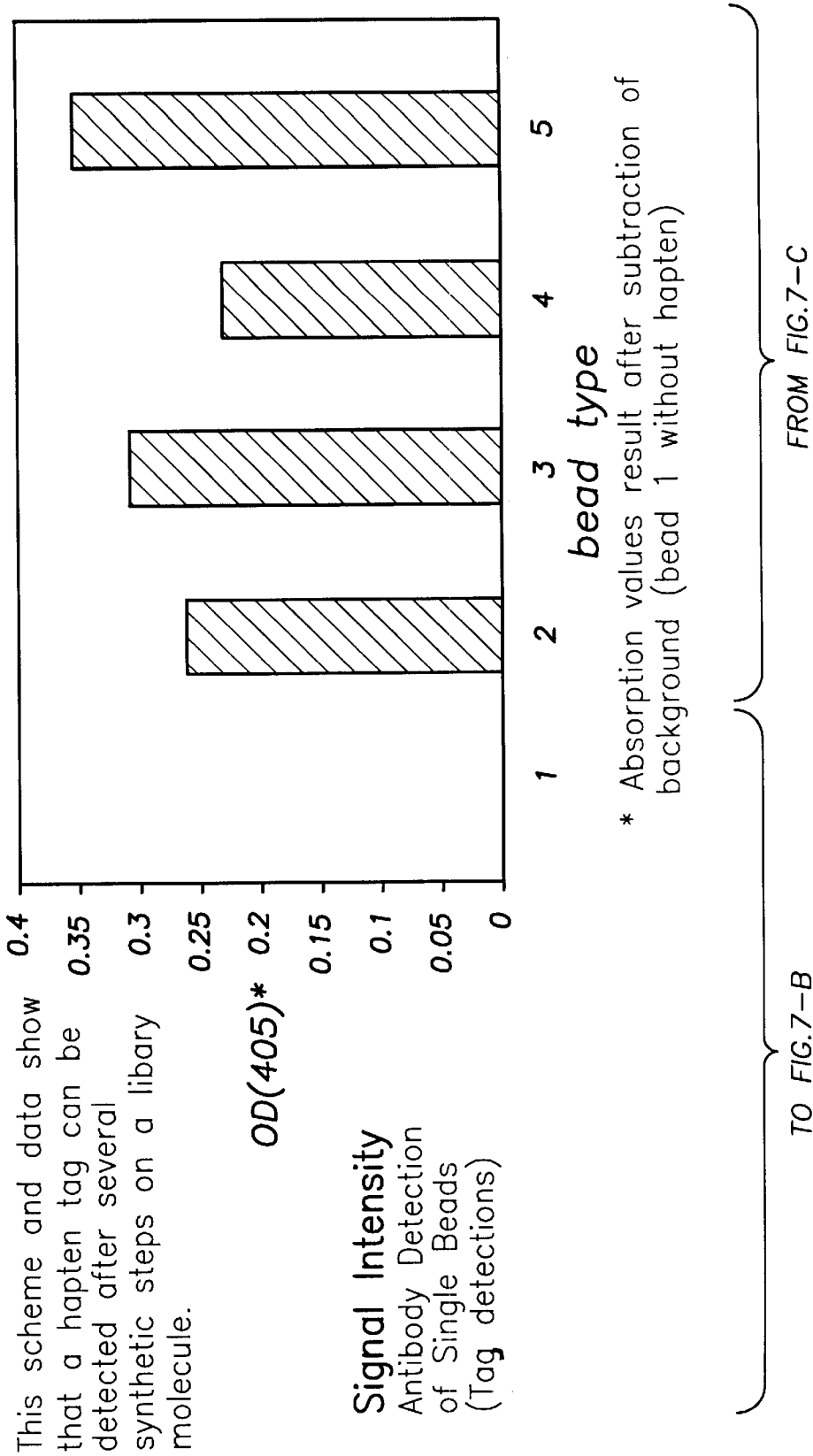

FIG. 7-B
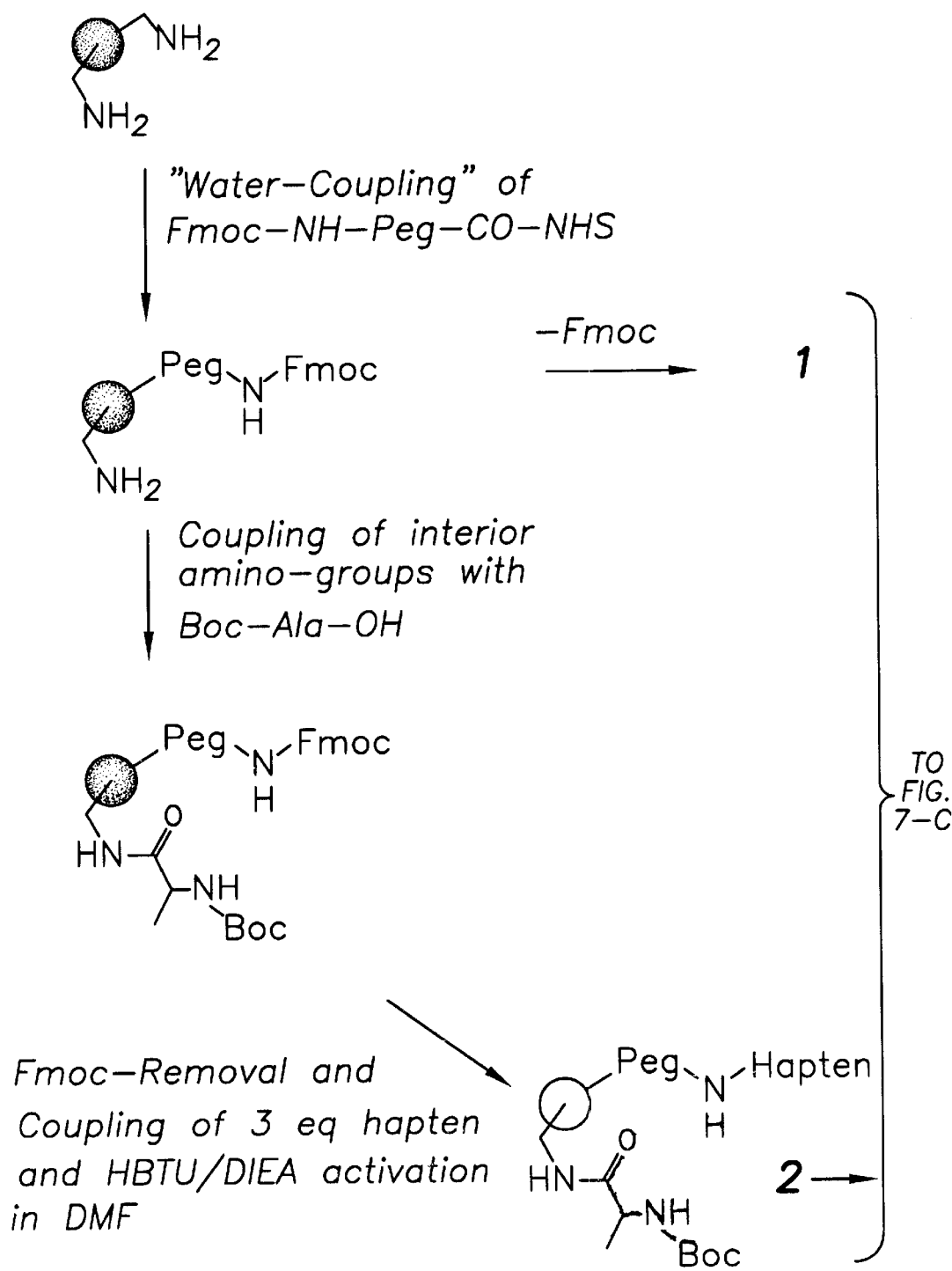

FIG. 7-C
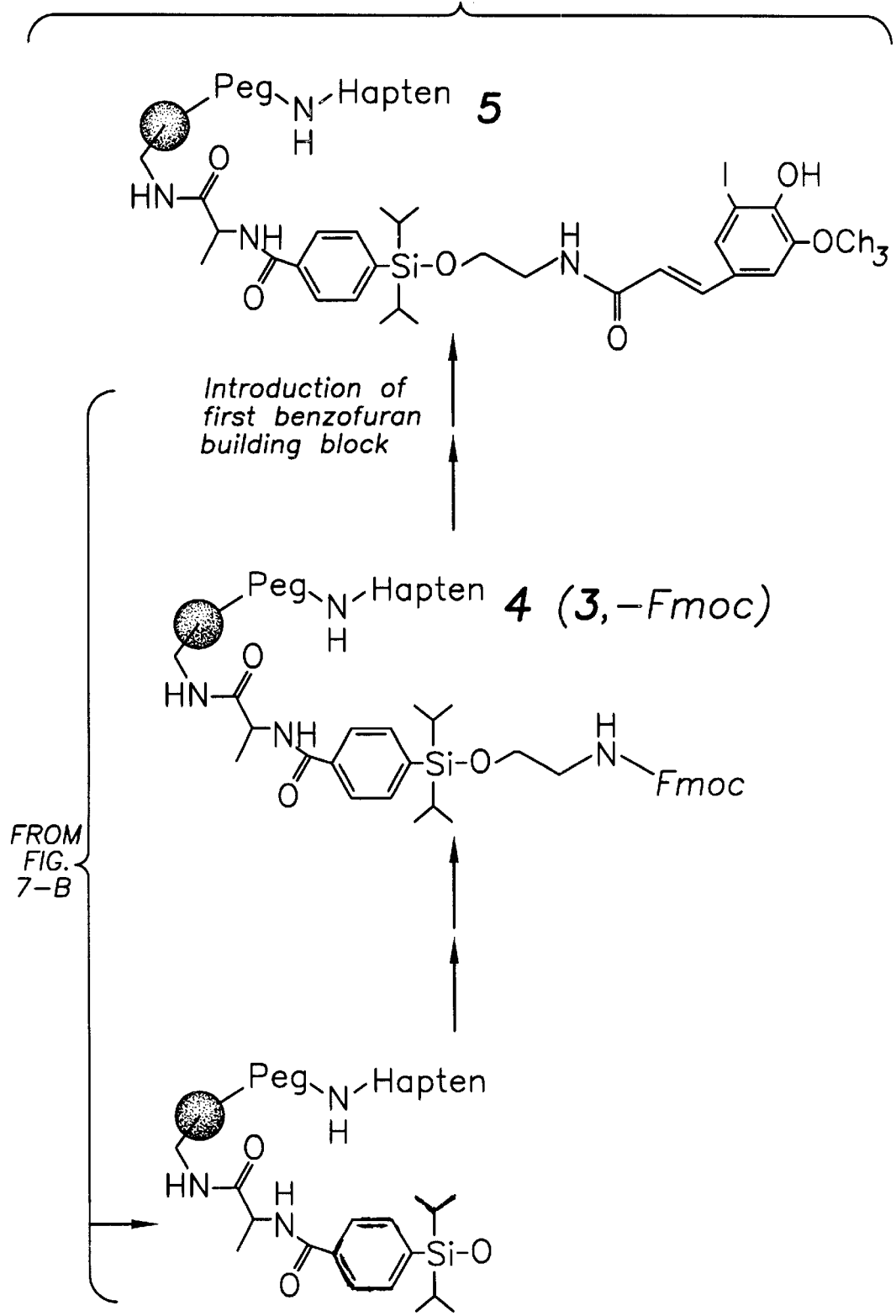

DETECTING STRUCTURAL OR SYNTHETIC INFORMATION ABOUT CHEMICAL COMPOUNDS

This application claims the benefit of U.S. Provisional application Ser. No. 60/109,725, entitled "Detecting Structural or Synthetic Information about Chemical Compounds", filed Nov. 23, 1998, which is incorporated herein by reference.

GOVERNMENT SUPPORT

The work described herein was supported by National Cancer Institute grant number CA78048. The United States may have certain rights in this invention.

BACKGROUND OF THE INVENTION

The goal of pharmaceutical chemistry has always been to identify chemical compounds that have the ability to affect specific biological pathways or reactions so that they are useful as therapeutic agents or as probes of biological activity. Recent developments in synthetic chemistry have greatly expanded scientists' ability to rapidly produce potentially interesting chemical compounds, and to assay their biological and chemical activities. Most notably, the burgeoning field of combinatorial chemistry provides techniques for the rapid and facile generation of large numbers of compounds (see, e.g., "Combinatorial Chemistry", *Chem. and Eng. News*, Feb. 24, 1997, p. 43; Thompson, L. A., Ellman, J. A., *Chem. Rev.* 1996, 96, 555).

Combinatorial methods are available for use in the solution phase, the solid phase, or combinations thereof. One particularly powerful solid-phase technique, known as "split and pool" synthesis, allows large numbers of compounds to be produced, each of which is separately attached to its own solid support (Furka, A. et al., *Int. J. Pept. Protein Res.* 1991, 37, 487–493). However, one complication of this method is that, because the solid supports are recovered as mixed pools, either deconvoluting or encoding strategies are required to determine the chemical structure of compounds with desired activities.

A large variety of different deconvolution and encoding techniques have been developed to facilitate the analysis of chemical compounds produced by split-and-pool techniques (See, e.g., Czarnik, A. W., *Curr. Op. Chem. Biol.*, 1997, 1, 60). One of the earliest encoding methods employed oligonucleotide tags for identification of libraries of random oligomers (WO 93/06121). Although an advantage of this method is that tag analysis can be readily accomplished through polymerase chain reaction amplification (PCR), the tags are not sufficiently stable to survive the synthetic conditions required for production of small molecule libraries.

Other available encoding schemes include the use of fluorophenyl ether tags (Ohlmeyer et al., *Proc. Natl. Acad. Sci. USA* 1993, 90, 10922; Nestler et al., *J. Org. Chem.* 1994, 59, 4723). These tags have the advantage that they are resistant to most of the reaction conditions used for organic synthesis. However, the tags are analyzed by gas chromatography and electron capture, and therefore cannot be assayed without first being cleaved from the solid support. Difficulties are often encountered in attempts to analyze the small quantities of tag that are released in these methods.

There has been one report of a tag compound, 3,5-dimethoxy benzoic acid labeled with $^{13}$C, being analyzed directly on a solid support (a Wang resin), without first being released by cleavage (*J. Am. Chem. Soc.* 1996, 118, 2305; WO 97/14814). However, the method described lacked sensitivity, and required time-intensive $^{13}$C nuclear magnetic resonance (NMR) spectroscopy techniques. Unfortunately, the technique therefore cannot be practically applied to the rapid analysis of large numbers of compounds.

Therefore, there remains a need to develop an improved system for encoding reaction history or direct structural information about chemical compounds synthesized on the solid phase. Preferably, the system should allow on-bead analysis, and should employ chemically robust detectable tags.

SUMMARY OF THE INVENTION

The present invention provides an improved system for encoding the reaction history and/or molecular structure of chemical compounds attached to a solid support. In general, the invention provides an identification unit comprising a binding pair in which a first ligand, component one, is associated with the solid phase, and a second ligand, component two, is employed to specifically recognize the first ligand. Component one need not be separable from the solid support. Component one is sometimes referred to herein as the "tag".

In certain preferred embodiments of the invention, component one is attached to the solid phase during the synthesis of the chemical compound. In such circumstances, component one preferably designates a particular reaction step so that the synthetic history of the chemical compound is recorded in a series of component ones attached to the solid support. Each component one is then preferably detected by means of its component two binding partner, after the synthesis is complete.

Component two may be any ligand capable, of specific interaction with a component one. Component two need not be chemically robust, as it is not present during the synthesis reactions. However, component two must be selected so that its interaction with component one is detectable. Any method of detection is sufficient. For example, component two may include (i.e., may be covalently linked to) or be otherwise associated with (i.e., by other than covalent linkage) a fluorescent, luminescent, or radioactive moiety. In certain preferred embodiments, component two is associated with a detectable moiety such as a nucleic acid molecule (having a selected nucleotide sequence defining a particular component one-component two interaction) whose signal is subject to amplification (e.g., by PCR), so that the detectable moiety can be identified even when present at very low levels. The steps involved in detecting this binding interaction preferably include, (1) providing a solid phase, a chemical compound and a tag, (2) contacting the tag with the binding partner, and (3) detecting a detectable moiety, which detectable moiety may be any moiety capable of being identified.

The present invention also provides methods of identifying chemical compounds attached to a support by (1) providing a solid support to which a chemical compound whose structure is to be determined is attached, along with a tag selected to represent a structural or synthetic feature of the chemical compound; (2) contacting the solid support with a binding partner that binds specifically and detectably to the tag; and (3) detecting binding of the binding partner to the tag, the existence of such binding being indicative of the presence of the tag on the solid support, which presence is in turn indicative of the existence of the structural or synthetic feature of the chemical compound. Preferably, (1) the step of providing involves providing a solid support comprising a plurality of attached tags, each of which is selected to represent a particular structural or synthetic feature of the chemical compound; (2) the step of contacting comprises (a) providing a plurality of binding partners, each of which specifically and detectably binds to one tag; and (b) contacting the solid support with each of the binding partners (simultaneously or sequentially); and (c) the step of detecting comprises detecting each binding partner/tag binding interaction, and thereby determining the existence of the structural or synthetic features of the compound.

Finally, the present invention provides methods for analyzing the tags off the bead. Specifically, the present invention provides techniques for creating spatially encoded split and pool libraries using the tags and binding partners described herein. According to this aspect of the present invention, (1) the beads, with attached compounds and tags, are distributed into microtiter plates at one bead per well; (2) the tags are detached from the beads by a specific releasing chemistry; (3) the tags are arrayed onto a slide; and (4) the compound represented by the tags are identified by the steps comprising (a) providing a plurality of binding partners; (b) contacting the tags arrayed on each slide with each of the binding partners; and (c) detecting each binding partner/tag binding interaction.

In another aspect, the present invention provides a kit comprising (1) a collection of chemically robust tag components capable of attachment to a solid support, and (2) a corresponding collection of detectable binding partners, each of which interacts selectively with one tag component.

Definitions

"Encoded combinatorial library" An encoded combinatorial library, as that phrase is used herein, is a collection of chemical compounds where each compound is attached to a solid support that also contains information revealing the structure of the compound, either directly or by recording the reaction history that produced the compound.

"Tag": As used herein, the term "tag" means a chemical moiety, preferably a robust, small molecule that is capable of being detected by a binding partner moiety when present at less than or equal to $10^{-12}$ moles on the bead. This property renders the tag detectable and optionally may provide the property of rendering the tag identifiable while attached to a solid support.

"Chemically robust": The term "chemically robust", as used herein, in reference to a tag, means that the tag can withstand the chemical reactions utilized in the synthesis of combinatorial libraries.

"Small molecule": As used herein, the term "small molecule" refers to an organic compound either synthesized in the laboratory or found in nature. Typically, a small molecule is any organic molecule that can preferably be recognized by a macromolecule, and has a molecular weight of less than 1500. For example, the small molecule could be a hapten.

"Binding partner": As used herein, the term "binding partner", "binding partner moiety", "partner", or "partner molecules" refers to a compound or compounds capable of selectively and specifically associating with the tag component as a means to identify the tag component. A binding partner can be any compound that interacts specifically with the tag such that together they form a binding pair or identification unit. In one non-limiting example, a binding partner may be an antibody that specifically recognizes the small molecule tag. It is preferable that the binding partner has associated with it some means of detecting the antibody.

"Label": As used herein the term "label", or "detectable moiety" is any means for detecting an interaction between a tag and a binding partner, thereby identifying the presence of the tag and the existence of the structural or synthetic information that the tag represents. The label may be any means of detection that can be assayed. The label provides a "signal" indicating which tag is being identified. In one non-limiting example, the label may be a fluorescent label associated with a binding partner.

"Signal": The term "signal" as used herein refers to the information readout provided by the identification unit. The readout may indicate which tag is being identified. The signal may be provided by the label. In some preferred embodiments the signal is provided by a fluorescent label or a quantum dot. In other preferred embodiments the signal is provided by a nucleic acid. In yet other preferred embodiments, the signal is provided by the binding partner itself, for example where the binding partner is an identifiable nucleic acid.

"Identification unit": The term "identification unit" as used herein, refers to the binding pair comprising a tag component and a binding partner moiety that together function to encode information. In one preferred embodiment, the identification unit includes a small molecule tag and any compound capable of associating specifically and detectably with that small molecule. In another preferred embodiment the identification unit includes a small molecule tag and an antibody capable of selectively associating with that small molecule. Preferably, the tag is attached to a solid support and the binding partner, with its associated means of detection, be associated with the small molecule on the solid support. Alternatively, the tag may be cleaved from the solid support for the purpose of detection.

"Handle": "Handle" as used herein, refers to the chemical group or linker molecule used to attach a tag molecule to a glass slide or plate for creating spatially encoded split and pool libraries. A handle can be any chemical moiety capable of attaching any tag to a slide (preferably glass) also modified for attachment. Preferably, the chemical moiety is easily attached to the tag. For example, a glass slide may be derivatized with either thiol or maleimide groups to covalently capture a tag molecule via an attached thiol group.

"Choice": As used-herein the term "choice" means the alternative variables for a given stage in a combinatorial synthesis, such as reactant, reagent, reaction conditions, and combinations thereof. The term "stage" refers to a step in the sequential synthesis of a compound or ligand; the compound or ligand being the final product of a combinatorial synthesis.

"Associated with": The term "associated with", as used herein, is defined as using any means of providing physical proximity between two compositions of interest (e.g., covalent association, hydrophobic interaction, or ionic interaction). By way of example, a tag may be associated with its binding partner.

"Linker": As used herein, the term "linker" means a chemical moiety that can simultaneously attach to both a solid support and a tag, thereby "linking" the tag to the support. Optionally, the linker may be cleavable so that the tag may be released from the solid support by disruption of the linker. These three properties may be embodied in a single chemical structure. A linker may be embodied in a single chemical moiety, or in a collection of chemical moieties associated with one another. In this latter case, one of the chemical moieties provides the property of rendering the linker attachable to the solid support; the second chemical moiety, provides the property of rendering the linker cleavable; and the third chemical moiety provides the property of rendering the linker attachable to the tag. Desirably the chemical structures that provide a means for tag attachment and a means for tag cleavage are one and the same.

"Cap" or "Capped": As used herein, the term "cap" or "capped," as used in reference to applying a tag to a reaction series, means to terminate the growing reaction series with the added tag.

"Support": The materials upon which the combinatorial syntheses of this invention are performed are referred to herein interchangeably as beads, solid surfaces, (solid) substrates, particles, (solid) supports etc. These terms are intended to include:

a) solid supports such as beads, pallets, disks, capillaries, hollow fibers, needles, solid fibers, cellulose beads, pore-glass beads, silica gels, polystyrene beads optionally cross-linked with divinylbenzene, grafted co-poly beads, poly-acrylamide beads, latex beads, dimethylacrylamide beads optionally cross-linked with N,N'-bis-acryloyl ethylene diamine, glass particles coated with a hydrophobic polymer, etc., i.e., a material having a rigid or semi-rigid surface; and b) soluble supports such as low molecular weight non-cross-linked polystyrene.

"Specifically associates": as used herein in reference to the interaction between a tag component and a binding partner means that the interaction between one tag component and a specific binding partner occurs preferably over interaction with a variety of other binding partners. For example, tag A is presented with binding partners A–Z, but only binds to binding partner K. In this example, tag A "specifically associates" with binding partner K.

DESCRIPTION OF THE DRAWING

FIG. 1. A photograph depicting detection of hapten tags on TENTAGEL bead using an antibody.

FIG. 2. The chemical structures of a set of bi-aryl amides with an amino hexanoyl spacer for matrix attachment.

FIG. 3. An example of a inventive variable hapten for antibody binding with an acid cleavable resin attachment site and a protected thiol for capture on glass.

FIG. 5. The chemical structures of fourteen hapten tags which were synthesized, and to which antibodies were raised.

FIG. 6. A scheme showing the synthesis of the hapten tag on the outside of the bead and the library of compounds on the inside of the bead.

DESCRIPTION OF CERTAIN PREFERRED EMBODIMENTS

Figure 4:
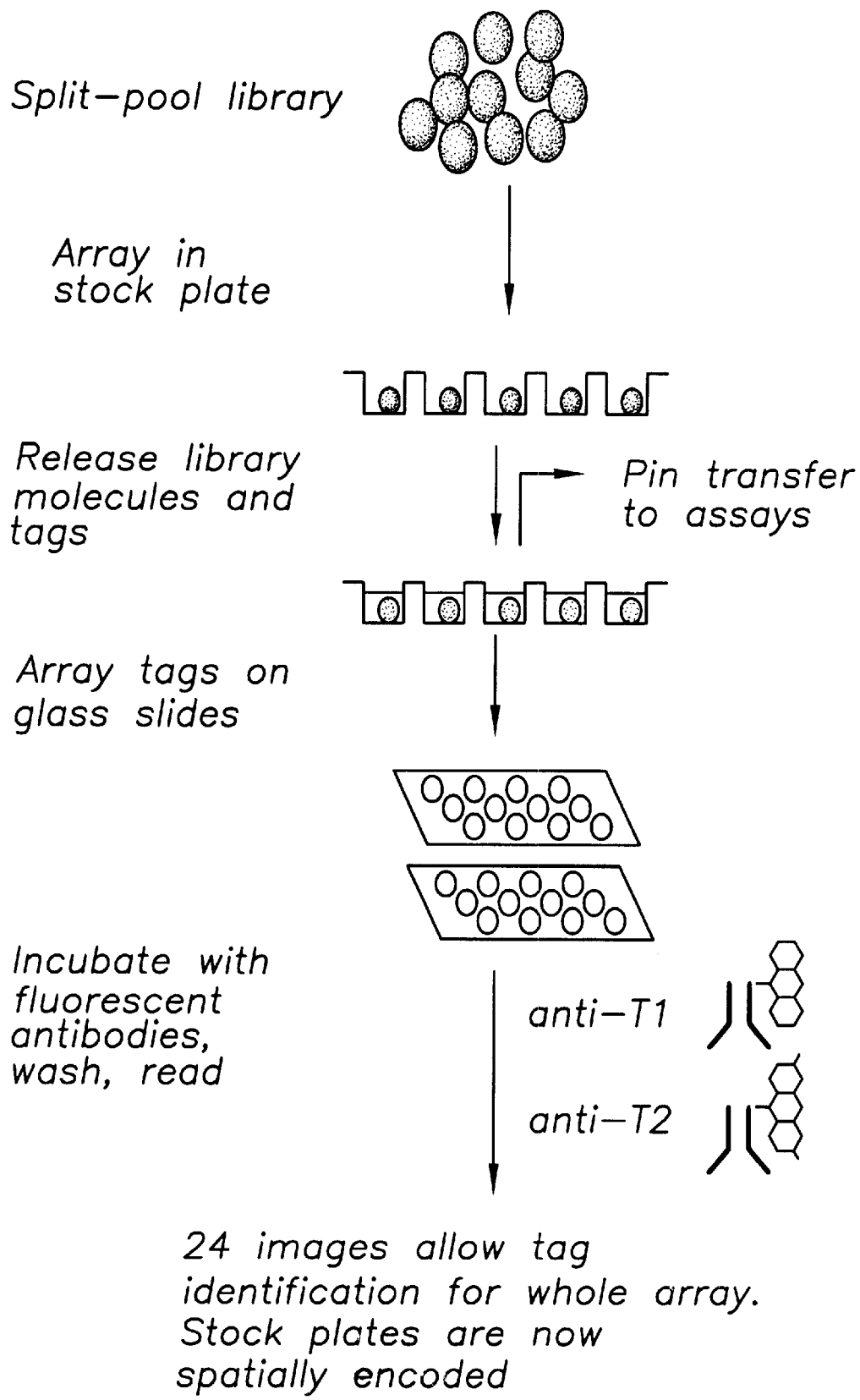
FIG. 4. A flow chart representing a method of spatially arraying tags on glass slides and analyzing the fluorescent signal.

Recognizing the need for the facile and rapid identification of the large numbers of compounds generated in combinatorial synthetic methods, the present invention provides an improved flexible system for the rapid and non-destructive analysis of tags that encode structural or reaction history information relating to a chemical compound attached to a solid support. This improved system and method preferably utilizes chemically robust tags, and thus provides significant flexibility in a desired synthesis. Certain preferred embodiments also provide a decoding technique that is capable of amplification, so that small quantities of tags may be analyzed according to the inventive system and method.

In general, the invention provides an identification unit, comprising a tag component and a binding partner, that readily records information relating to the particular structure or synthetic history of a chemical compound. As discussed above, component one comprises a tag that is capable of attachment to a support unit, and is selected to represent a particular chemical structure, reaction stage, or reaction choice relevant to the compound of interest. It is particularly preferred that the tag component be chemically robust in that it is resistant to the reaction conditions employed in the synthesis of the chemical compound to which it refers.

Component two comprises a binding partner capable of specifically and detectably associating with the tag component, and thus providing a means for the identification of the tag component. Because decoding of the reaction information is preferably carried out after the molecule is made, the binding partner need not be a chemically robust molecule.

Various characteristics of the tags and binding partners utilized in preferred embodiments of the present invention are discussed in more detail below; certain examples of inventive compositions for use in the method of the present invention are also presented.

Tags

The tags of the present invention record information about the compound attached to a solid support. Any information may be recorded by the tag. In one preferred embodiment, the information recorded by the tag is structural information (e.g., a particular tag is selected to represent a chemical moiety, such as a phenol group). In another preferred embodiment, the information recorded by the tag is functional information (e.g., a particular tag is selected to represent an activity, such as DNA-binding capability). In yet another preferred embodiment, the information recorded by the tag is reaction history (e.g., a particular tag is selected to represent a reaction step performed during the synthesis of the compound). As one of ordinary skill in the art will realize, the tag may represent a particular choice of reactant, or alternatively may represent both a particular choice of reactant and the particular stage at which that reactant is added. Preferably the information recorded is reaction history.

Those skilled in the art will recognize that a binary encoding scheme may be utilized to record reaction history, whereby the presence or absence of a particular tag may be associated with a particular reaction stage or compound. It is also well known by those skilled in the art that higher order encoding schemes may be employed whereby the presence of, absence of, or distinguishable state of (e.g., concentration) a tag can be utilized to encode the chemical synthesis. An advantage of higher order codes over a binary code is that fewer identifiers are required to encode the same quantity of information about the synthesis.

The tags selected for use in the present invention must also be detectable by specific interaction with a binding partner. The present invention provides an identification system that relies on the recognition of the tag by a binding partner that may then be detected in order to decipher the information recorded by the tag. Binding partners are discussed in greater detail below.

As mentioned above, the tag components are preferably used to record reaction history. The tag is preferably attached to a solid support on which the synthesis occurs. Synthetic reactions are often harsh in nature. Therefore, if added to a solid support during a chemical synthesis, the tag component must be a chemically robust molecule. Preferably, these chemically robust tags are capable of withstanding the often harsh reaction conditions that are employed in the synthesis of desired compounds on the solid support. Furthermore, because the present encoding system comprises a binding pair, the small molecule tag (component one) also must necessarily be specifically recognized by a particular binding partner (component two), as can be readily determined by standard methods in the art. As one of ordinary skill in the art will realize, chemically robust molecules are comprised of particular chemical functionalities that are inert to the specific chemical reactions being employed for a particular synthesis. Thus, the selection of a particular functionality over another will depend upon the synthesis of the desired compounds. Exemplary chemically robust small molecules that can be employed a wide variety of chemical syntheses include, but are not limited to, compounds having aromatic functionalities, specifically fluorinated aromatic functionalities. FIG. 2 depicts examples of chemically robust small molecules that can be employed in the present invention.

Each tag component is not only preferably chemically robust, but also preferably comprises at least one functional group, preferably a common functional group, capable of facilitating the attachment of the tag to the surface of a particular solid support. As one of ordinary skill in the art will realize, the attachment of a tag to a solid support may be accomplished by any means available in the art. The use of a solid support in the synthesis of chemical compounds is particularly preferred because it enables the use of more productive split and pool techniques to generate libraries of encoded compounds containing as many as or more than 1,000,000 members. The use of a solid support is advantageous for the synthesis of libraries because the isolation of support-bound reaction products can be accomplished simply by washing away reagents from the support-bound material and therefore the reaction can be driven to completion by the use of excess reagents (Tan et al., *J. Am. Chem. Soc.*, 1998, 120, 8565).

Preferred solid supports include any material that is an insoluble matrix and can have a rigid or semi-rigid surface. Exemplary solid supports include, but are not limited to pellets, disks, capillaries, hollow fibers, needles, pins, solid fibers, cellulose beads, pore-glass beads, silica gels, polystyrene beads optionally cross-linked with divinylbenzene, grafted co-poly beads, poly-acrylamide beads, latex beads, dimethylacrylamide beads optionally crosslinked with N,N'-bis-acryloylethylenediamine, and glass particles coated with a hydrophobic polymer. One of ordinary skill in the art will realize that the choice of a particular solid support will be made keeping in mind the compatibility of the solid support with the reaction chemistry being utilized. In one particularly preferred embodiment, a TENTAGEL (TENTAGEL is a trademark of Rapp Polymere GmbH and describes a family of resins which are grafted copolymers consisting of a low crosslinked polystyrene matrix on which polyethyleneglycol (PEG or POE) is grafted) amino resin, a composite of (1) polystyrene bead crosslinked with divinylbenzene, and (2) PEG (polyethylene glycol), is employed for use in the present invention. TENTAGEL is a particularly useful solid support because it provides a versatile support for use in on-bead or off-bead assays, and it also undergoes excellent swelling in solvents ranging from toluene to water.

The tags of the present invention may be attached directly to the solid support, or may be attached to the solid support through a linking reagent. Direct attachment of the tags to the solid support is preferred because it allows direct on-bead analysis of compound structure or reaction history. Alternatively, the use of a linking reagent may be useful if facile cleavage of the tags of the inventive encoding system is desired, for off-bead analysis of the compound structure or reaction history.

In one particularly preferred embodiment, direct attachment of the tags to a polystyrene or TENTAGEL bead may be effected preferably by taking advantage of rhodium catalyzed carbene chemistry to promote attachment to the polystyrene backbone via C-H insertion (Nestler et al., *J. Org. Chem.* 1994, 59, 4723). As but one example, a tag component containing, or being modified to contain, a diazoketone moiety (for example, conversion of a benzoic acid derivative to a diazoketone) can be attached to a solid support using rhodium catalyzed carbene chemistry. In another particularly preferred embodiment, direct attachment of the tags to a glass bead may be effected by reaction of a glass bead with a methoxy silane moiety on the tag component (For examples of chemistry on glass surfaces, see, e.g., Plueddemann, E. P. *Silane Coupling Agents*, Plenum Press: New York, 1991; Hertl, W., *J. Phys. Chem.* 1968, 72, 1248; Dreyfess, P. et al., *Macromolecules* 1978, 11, 1036), or may be attached to a modified glass surface as shown in FIG. 3.

The tag may be added to the solid support during the synthesis of a compound or a library of compounds by any of a variety of mechanisms. In one embodiment, tags are chosen for their ability to terminate a growing synthetic chain. Such a tag can be used to cap a small percentage of growing synthetic chains at by adding to the reaction mix, a low concentration of the tag component. For example, reaction A may be capped by tag A by the incorporation of tag A onto the compound at a specific stage in the reaction series. Utilization of this technique provides that a small percentage of reaction A products are terminated by tag A, which can be detected in the decoding process.

Alternatively, the tag may be coupled to a solid support through a unique set of sites using orthogonal protection. In this method, the support unit is functionalized with more than one reactive group, and most preferably is functionalized with two reactive groups. In this fashion, addition of the tags to the bead must be employed by deprotecting a specific number of sites for reaction to take place. In one embodiment, each tag occupies a small fraction of sites on the bead. For example, a bead that has been exposed to a series of chemical reactions to synthesize a compound, the chemical reaction sequence being reaction A, reaction D, and reaction F, approximately a third of the linkage sites occupied by tags would be occupied by each of tag A, D, and F. Alternatively, one of the tags may occupy a small fraction of linkage sites on the bead and subsequent tags may be added to the first tag as a growing linear chain. For example, instead of a fraction of linkage sites being occupied by tags A, D, and F, as in the above example, all of the linkage sites would be occupied by tag A. Tags D and F would added sequentially to tag A. According to the teachings of the present invention, tags are preferably connected in such a manner to allow association of each tag with its respective binding partner.

Another preferred embodiment provides tags that are attached at random positions on the solid support, preferably directly using carbene insertion chemistry as discussed above. The advantage of attaching the tag directly onto the solid support is that incorporation of the tag into the reaction product is avoided. Such incorporation can be inhibitory to identifying positively interacting tags during subsequent screening of the library. Furthermore, this technique eliminates the need to use more complex and time-consuming orthogonal protection schemes as described above.

In above mentioned embodiments, where the tags are linked directly to the bead surface, it is preferable that the fraction of sites occupied by the tags be significantly less than the fraction of sites occupied by the compound, such that the compound be present in sufficient quantity to be assayed by any of a variety of techniques. It may be desirable to maximize the number of sites used for attachment of the compound, while maintaining a sufficient quantity of tag linkage sites that are adequate for the purposes of signal detection in the decoding process. In particularly preferred embodiments, coupling of the tag molecules occurs at the level of 0.1 to 0.001% of bead chemistry. In most particularly preferred embodiments, coupling of the tag molecules occurs at the level of 0.01% of bead chemistry. Alternatively, in the case of carbene insertion chemistry, the fraction of sites occupied by tags is not so much of a concern, but using a high number of tags can destroy the compound being synthesized by insertion of the tag into the compound.

In yet another preferred embodiment of the present invention, compound synthesis is carried out on the inside of the support. A particularly preferred support for use in this manner includes TENTAGEL beads. Because TENTAGEL beads may undergo significant swelling in solvents, reagents for use in the synthesis of compounds and libraries of compounds may react inside the support. The tag may then be selectively linked to the outside of the bead by using a bulky reagent to deprotect or to catalyze tag addition to the surface. In preferred embodiments, the bulky reagents include, but are not limited to, enzymes, catalysts, and polymers. Therefore, by having the chemical compounds of the library on the inside of the bead, the synthetic chemistry is protected from interaction with the binding partner. This minimizes the chance of spurious recognition of non-tag moieties by the binding partner. Having the tag coupling separated from the combinatorial coupling reactions also provides the advantage of utilizing every linkage site available on the inside of the bead for combinatorial chemistry and eliminating the potential wasting of sites by the addition of multiple tags to those linkage sites. Additionally, placing linkage sites on the outside of the bead ensures their availability for interaction between the tag and the binding partner and/or their availability for amplification One of ordinary skill in the art will realize that the above-mentioned embodiments are not intended to be limiting; rather all equivalents are intended to be included within the scope of the invention.

Detection of the Tag

In preferred embodiments according to the above mentioned methods, the invention provides a binding partner capable of recognizing and binding selectively to the specific structure of each tag, wherein said tags are attached to the support unit. The binding partner, according to the present invention, can be any molecule capable of specifically and detectably recognizing a tag to form a binding pair. The binding partner need not be a robust molecule, because the decoding process occurs only after the synthetic steps are complete.

In one preferred embodiment, the inventive partner molecules are nucleic acids such as RNA or DNA. The nucleic acid molecules may be single stranded or double stranded in nature. Particularly preferred are single stranded RNA molecules. It has been demonstrated that single stranded RNA molecules can fold into a tertiary structure that is capable of binding to an organic small molecule (Ellington, *Current Biology*, 1994, 4, 427; Jenison et al., *Science*, 1994, 263, 1425; Davis et al., *Nucleic Acids Research*, 1996, 24, 702–706; Klugh et al., *Molecular Biology Reports*, 1994, 20, 97–107). In a particularly preferred embodiment the nucleic acid molecule may be amenable to amplification (e.g. via PCR) as a means to detect a very low quantity of identification unit associated with the solid support. A particular advantage of this system is that it provides a highly sensitive system for the detection of an identification unit associated with a solid support. The aspect of amplification provides a system in which the quantity of identification unit associated with a solid support does not limit the signal provided by the identification unit.

In other preferred embodiments, the binding partner may be a protein, a sugar or a chemical (e.g., other biological macromolecules, oligosaccharides, and synthetic receptors). Preferably, the partner molecule is any protein that recognizes the tag. By way of example, the protein may be an enzyme that binds to a specific small molecule, (e.g., an enzyme that binds to a small molecule inhibitor of enzyme function). In a most preferred embodiment, the protein is an antibody that recognizes a small molecule specifically.

A variety of methods are available in the art for the generation of antibodies for use in the present invention (See for example Harlow and Lane, "Antibodies, a Laboratory Manual", Cold Spring Harbor Laboratory, 1988, incorporated herein by reference). For example, polyclonal antisera can be generated by immunizing an animal, such as a rabbit, with the antigen of interest (e.g., the tag or a tag mimic) and collecting sera from the immunized animal after an immune response has been mounted. In particularly preferred embodiments, the antigen is a small molecule. Polyclonal antisera contain many antibodies that recognize multiple epitopes on the antigen. Once the polyclonal antisera is collected, one may select out the antibody of interest by affinity purification. For example, the polyclonal antibody may be applied to a chromatography column containing the antigen of interest. The antibodies that bind specifically to the antigen on the column will adhere to the column as a means for selecting out the antibodies with high affinity for the antigen. These antibodies may then be collected and used as binding partners in the decoding process.

In a preferred embodiment, the present invention teaches that monoclonal antibodies may be generated for use as binding partners. Monoclonal antibodies are generated from a single clonal cell line isolated from an animal immunized with the antigen of interest. Monoclonal antibodies recognize a specific epitope on the antigen. Therefore the need to affinity purify the antibody is averted. In other preferred embodiments, recombinant antibodies can be created such that the specificity of the antibody is engineered into the antibody protein and a recombinant protein is generated with that desired selectivity (See Harlow and Lane, supra; Sambrook et al., Molecular Cloning: A Laboratory Manual, Cold Spring Harbor Press, N.Y., incorporated herein by reference). Alternatively, antibodies to small molecules may be purchased. For example antibodies have been generated against the small molecule digoxygenin (see, Example 1) (Jacobsen and Schultz, *Curr. Opi. Struct. Biol.*, 5(6):818–24, December 1995).

As previously mentioned, the specific association of the binding partner unit and its corresponding tag enables decoding of the information represented by the tag (or collection of tags) attached to the solid support. Thus, the present invention requires the interaction between the tag and its binding partner be detectable. Any mode of detection is sufficient, for example, the tag may include a "masked" detectable moiety, or label. The label may be masked in such a way that it does not provide the detectable signal until it is reacted with a binding partner. For example, a tag may have hydrophilic moieties that would be amenable to normal chemical steps in the synthesis of a compound. These hydrophilic moieties may be protected during the chemical synthesis, and then deprotected once the synthesis is complete. The protective groups must be orthogonal. For example, a chemical protecting group for a hydrophilic moiety must not be altered or removed by the reagents used in the chemical synthesis. The chemistry used to remove the protecting group from the hydrophilic moiety must be different from the chemistry employed in the chemical synthesis so that one does not harm the other. Alternatively, the binding partner may include a label, so the association of the detectable label with the tag attached to the solid phase reveals the interaction between the tag and the binding partner. The detectable signal provided by the label may alternatively be produced by an interaction, for example a reaction between a specific enzyme and its substrate.

Preferably, the label is associated with the binding partner. The label may be any label that produces a signal capable of being detected. Particularly preferred labels are fluorescent, luminescent, or radioactive. The label may be any chemical, sugar, or protein. In other preferred embodiments, the label be amplifiable. Amplification provides the advantage of increasing the detectable signal provided by the label. The aspect of increasing the signal provided by a particular identification unit used to decode a library of compounds provides a significant advantage over other systems of decoding chemical libraries in that it provides a greater sensitivity of detection. One example of an amplifiable label is a nucleic acid. In a particularly preferred embodiment of the present invention, a binding partner is labeled with an amplifiable nucleic acid molecule. Methods and reagents for labeling binding partners and amplifying the signal provided by the labels is described in more detail below.

Another advantage of this invention is that the detectable signal can be collected while the tag is still on the bead. This aspect of the invention provides an advantage over decoding methods that require removal of the tag prior to identification of the tag by providing convenience and rapidity of analysis. Rather than removing the tags from each bead and subjecting the collection of removed tags to a decoding assay, the step of removing the tags is eliminated. This technique further provides the advantage of avoiding exposure of the reaction products and the tags to the chemical treatment required to remove the tags from the beads. Another valuable aspect of this invention is that less of the surface area on the bead may be used for the chemical tag. This aspect permits the use of smaller beads if necessary to the application at hand.

The present invention provides a variety of mechanisms for detection of binding partner/tag interaction. In general, it will be recognized that non-specific binding of the binding partner to the tags on the bead may generate a high level of background signal. It may be necessary to increase the specificity of the binding interaction by adding all the other tags, excluding the tag being probed for, in the association reaction in order to compete nonspecific binding of the binding partner to any tag on the bead.

One preferred embodiment of the present invention provides a binding partner that includes a fluorescent label that can be used to detect the identification unit on the bead. In one particular embodiment, the fluorescent label emits a particular wavelength specific to a particular tag as a means to identify the tag recognized by the binding partner. The label may be incorporated directly or indirectly into the binding partner. For example, the fluorescent label may be incorporated onto a primary antibody specific to the tag, or a secondary antibody which itself recognizes the primary antibody directed against the tag. Quantitation of the fluorescent signal may occur by use of fluorescence imaging. One method of quantitating a fluorescent signal is the use of flow cytometry. Flow cytometers were originally designed for detecting fluorescent signals off single cells and are therefore capable of detecting the fluorescent signal emitted from a single bead by passing a stream liquid droplets each containing a single bead through the detection unit in series. Imaging of the signal emitted from the bead surface may be enhanced by the use of confocal imaging or some other optical section (e.g., a CCD camera).

In an alternative embodiment, the binding partner/tag interaction is detected by chemiluminescence. In one illustrative example, a molecule capable of generating chemiluminescent emissions when provided with a substrate is associated with the binding partner. After the binding partner is contacted with the tag, the chemiluninescent substrate is added, and the reaction developed to allow detection of the identification unit. One example of a chemiluminescent system is the peroxidase system (see Ausubel et al., supra).

In this example, the binding partner is an antibody. The fluorescent signal is collected from the bead before the binding partner has been applied to the bead. This signal represents the background fluorescent signal emitted from the bead. The fluorescently labeled antibody specific for tag A is then added and allowed to associate with tag A attached to the beads. After association, the beads are washed with a detergent solution to destroy any non-specific antibody/tag interactions. The washed beads are applied to the flow cytometer device and the fluorescent signal from each bead is collected in series, over time. The fluorescent signal representing tag A is collected from each bead and compared to the background signal. Any detected signal significantly above the background signal for tag A indicates that the bead has tag A and thus identifies a reaction choice and stage of reactant addition used in the reaction series applied to that bead (see Example 4).

In an alternative embodiment, the binding partner specific to tag A is allowed to associate with the bead, the beads are washed, and a secondary binding partner coupled to a fluorescent label is added that recognizes the tag A specific antibody binding partner. The beads are washed again and the label detected as before. Whether the primary antibody binding partner or the secondary antibody binding partner is labeled, the fluorescent signal representing tag B, tag C, tag D, etc. is measured until a reaction profile for each bead is obtained defining the chemical structure on that bead. For example, bead number one may display a profile identifying a positive signal for tags A, C, and F, indicating that in a three reaction series, reaction monomers A, C, and F were added in a sequence defined within the identity of the tags (see Example 5).

In yet another preferred embodiment, the binding partner/tag interaction is detected through use of a nucleic acid label. A particularly preferred embodiment of the present invention provides nucleic acid labels that are incorporated into a binding partner as a means of detecting the identification unit. The nucleic acid molecule may have particular characteristics specific to a particular tag as a means to identify the tag recognized by the particular binding partner. According to the present invention, the nucleic acid may be DNA or RNA. Preferably the nucleic acid is DNA. The DNA may be single stranded or double stranded. Preferably, the DNA is double stranded because double stranded DNA is more stable. For example, one strand of the double stranded DNA may be attached to the binding partner and the other strand used in the polymerase chain reaction for amplification.

The DNA may be attached to the binding partner by any of a variety of methods. In one non-limiting example, DNA can be attached to a protein binding partner through association between biotin and streptavidin (Harlow and Lane, supra). Double stranded DNA may be labeled with biotin within one strand of the DNA. Biotin acts as a handle to attach to a protein binding partner labeled with streptavidin to the DNA. The high affinity interaction between biotin and streptavidin will hold the binding partner in tight association with the DNA tag. Alternatively, DNA may be attached to a protein binding partner through a disulfide bond. Of course, any system that forms an adequate association between the binding partner and DNA, so as to permit detection of the identification unit is within the scope of the present invention.

It will be appreciated by those skilled in the art that labeling the binding partner with DNA provides a tremendous advantage to this system because any DNA signal can be considerably amplified by using PCR (McPherson, "PCR: A Practical Approach", 1991, Oxford University Press, New York). The signal provided by the DNA label on the bead, therefore is not limited by the quantity of DNA that can be attached to a single bead. The polymerase chain reaction can amplify as much of a signal off a single bead as is necessary to detect the signal. The system may provide single molecule sensitivity. In one non-limiting example, one or more DNA labels are amplified directly off the identified bead and the amplified DNA is visualized on a gel. Alternatively, an RNA label is attached to the binding partner, the RNA is first reverse transcribed into DNA, and then the DNA is amplified by PCR. Thus, nucleic acid labels provide an advantage in instances where minimizing the quantity of tag on the bead is desirable (e.g., to facilitate screening of a combinatorial library).

A variety of bases are available by which different DNA labels (i.e., labels representative of different identification units) can be distinguished from one another. For example, such labels may have different nucleotide sequences and/or may be different lengths. In one particularly preferred embodiment, the length of the DNA label specifies the particular identification unit. Specifically, the length of the DNA molecule is used as a signal to represent the tag associated with the binding partner of the identification unit. For example, a collection of DNA labels are synthesized that vary in length, but have identical ends amenable to use with specific primers in a polymerase chain reaction. Each bead is placed in a separate reaction tube with the primers and the DNA labels representing multiple identification units are amplified. Once amplified, the DNA labels are loaded onto a sequencing gel next to a standard sizing ladder purchased from any supplier of molecular biological products or generated by a standard polymerase chain or sequencing reaction. The lengths of the variety of DNAs present in one reaction will identify the tags present on the bead of interest and thus define the compound attached to that bead.

Any of a variety of techniques available in the art may be used to visualize amplified DNA. The DNA may be visualized on an agarose gel by staining the gel with ethidium bromide. Alternatively, the DNA may be labeled. A variety of methods exist in the art to label DNA (see Sambrook et al., Molecular Cloning: A Laboratory Manual, Cold Spring Harbor Press, N.Y., incorporated herein by reference). The DNA may be labeled during the polymerization reaction by using primers that are labeled. For example, primers may be radioactively labeled, alternatively, primers may be fluorescently labeled. The DNA may also be end labeled.

In another preferred embodiment, the DNA labels have different nucleotide sequences, allowing them to be distinguished from one another. For example, in one particularly preferred embodiment, a collection of DNA oligonucleotides is generated that are identical in length, having common ends amenable to the polymerase chain reaction. The sequence of each oligonucleotide is identical except for varying the location of the first guanine nucleotide in the DNA sequence. Those of ordinary skill in the art will readily appreciate that not only the position of the first guanine, but the position of the first of any nucleotide may be varied. According to the present embodiment, once the DNA is amplified, rather than loading the DNA directly onto a sequencing gel, the amplified DNA is subjected to a sequencing reaction (see for example, Ausubel et al, "Current Protocols in Molecular Biology", Greene Publishing Associates, New York, vol. 1&2 1996, incorporated herein by reference) that contains a high concentration of dideoxy guanine. Those of ordinary skill in the art will recognize that dideoxy guanine terminates the reaction at the first guanine nucleotide, thereby generating a collection of different length DNA molecules whose size can be analyzed on a sequencing gel.

In an alternative embodiment, the sequencing reaction is carried out in the presence of all deoxyribonucleotides, excluding guanine, (i.e., in the presence of adenine, thymine, and cytosine), or whichever nucleotide is uniquely placed in each DNA label. The reactions without guanine, will terminate at the first guanine position for lack of a guanine nucleotide to add to that position. A parallel sequencing reaction can be run including all four nucleotides. The reactions containing all four nucleotides will not terminate until they reach the end of the DNA molecule. The reactions with and without guanine may be run adjacent to one another on a sequencing gel for comparison in order to determine the lengths of the amplified DNA molecules. As described above, the DNA may be visualized by labeling either the primer or the nucleotides.

Alternatively, different length DNAs are generated by placing restriction sites into the DNA sequence at different positions. Restriction digestion with the appropriate enzyme will generate different length DNA molecules whose size can be analyzed on a sequencing gel. In yet another embodiment, the presence or absence of a particular restriction site in a DNA molecule can be used to distinguish the DNA molecules from one another. Other non-limiting examples of identifying the nucleic acid tag include single strand conformation polymorphism, (see Ainsworth et al., Meth. Mol. Biol., vol. 31, pp. 205–210, 1994), and single strand length polymorphism, (see Detter et al., Nucleic Acid Res. vol. 26, pp. 4091–4093, 1998, or Tautz, Nuc. Acid Res., vol. 17, pp. 6463–6471, 1989).

In order to visualize the DNA on the sequencing gel, a fluorescently labeled deoxynucleotide can be used in the PCR reaction. Alternatively, a fluorescently labeled primer can be used in the PCR reaction with a deoxynucleotide that is not labeled. A separate sequencing reaction can be run in parallel to generate a one base pair ladder from a single base oligonucleotide linked to a fluorescent tag with a different fluorescent color. This reaction can be applied to the gel as a size marker to facilitate accurate size estimation of the DNA label.

As but one example of a preferred embodiment that employs nucleic acid labels, a bead containing a compound of interest and a collection of tags identifying that compound, is incubated with a panel of antibodies each of which binds specifically to a particular tag that might be on the bead, and each of which is associated with a particular DNA label. All DNA labels share a common sequence that can be used for simultaneous amplification. The bead is then washed with a stringent solution (See Harlow and Lane, supra) to remove antibodies that bind non-specifically to the tags on the bead but not the antibodies bound specifically to certain tags on the beads. After washing, the bead is subject to a polymerase chain reaction, with oligonucleotide primers corresponding to the common sequence located at the ends of the DNA label. The oligonucleotide primers, for, example, may be approximately 20 nucleotides in length. The particular DNA labels present are identified by their different lengths or sequences, (revealed, for example, through different restriction enzyme sites present in amplification product or different sizes of amplification products produced under certain conditions, etc.). Those of ordinary skill in the art will appreciate that multiple beads may be analyzed simultaneously.

Those of ordinary skill in the art will recognize that when, as described above, a nucleic acid molecule is employed as the binding partner, that molecule may simultaneously serve as the detectable label. Nucleic acids that bind to other compounds are known in the art as aptamers. Both RNA and DNA have tertiary structures capable of specific and high affinity binding to ligands (Ellington, 1994, supra; Jenison et al., 1994, supra; Davis et al, 1996, supra). Therefore, as discussed above, these nucleic acids may function as binding partners by recognizing a specific tag. The nucleotide length or sequence of the binding partner then serves as an inherent label, capable of identifying the identification unit. For example, specific RNA molecules have been identified that bind the amino D-arginine with a $K_d$ of 1.7 μm. Thus, where D-arginine is used as a tag, one such RNA molecule could serve as the binding partner and a label. As mentioned above, the sequence of the RNA molecule can be deciphered using reverse transcription, followed by amplification and sequencing of the DNA transcript. Using the nucleotide sequence as the label signal significantly expands the number of tags that can be identified using this system.

A panel of RNA or DNA aptamers that recognize specific tags may be synthesized and tested for their ability to bind specifically to a panel of tags. A process of affinity enrichment, also known as SELEX, may be used to select out only those aptamers that have a high affinity for a particular tag component (see, Klugh et al., *Mol. Biol. Reports*, 1994, 20, 97–107; Fitzwater et al., *Meth. Enz.*, 1996,267, 275–301). For example, random sequences may be synthesized and exposed to a particular tag. The aptamers that bind to the tag specifically may be amplified and the pool of amplified aptamers exposed to another round of binding to the tag to select for only those aptamers with specific, high affinity binding.

Thus, a variety of different labels may be employed in accordance with the present invention. In principle, any detectable label may be used. Furthermore, any effective detection means may be used to detect the label. Those of ordinary skill in the art will appreciate that certain labels may be analyzed by detection means that allow several different beads (i.e., beads to which different chemical compounds are attached) to be decoded in parallel (i.e., simultaneously). For example, the method of deciphering a DNA signal using the polymerase chain reaction to amplify the DNA signal and analyzing the amplified products on a gel is one example of a parallel method because it allows simultaneous analysis of multiple beads. Other means of detection can only analyze multiple beads in series. The method of detecting the fluorescent signal from an identification unit by flow cytometry is one example of a serial method.

Of course, one skilled in the art will recognize that the present invention is not limited to a process of decoding that requires that the tag remain on the bead. As discussed previously, the inventive tags may be attached via a labile linker which permits cleavage from the bead for analysis. Tags may be removed from the bead using reductive, oxidative, thermolytic, hydrolytic, or photolytic conditions depending on the nature of the linkage group. If it is desired to employ linkers for the inventive method, the use of photocleavable linkers is most particularly preferred because of the ability to use these linkers in vivo screening strategies. Once removed from the bead, the tag of the present invention is analyzed by providing the specific binding partner of this two component system and detecting the label associated with that binding partner.

A particularly preferred method for off bead analysis of tag information is a technique for spatially encoding the tag information after a complex chemical library is created by split and pool techniques. Libraries encoded by this technique will be referred to herein as "spatially encoded split and pool libraries" or (SESPLs). Spatially encoded chemical libraries have many advantages. In a spatially encoded chemical library, the identity of every compound is known, therefore the results of a screen contain much more information compared to screens in which only strong positive interactions are identified. It is also possible to screen a subset of a given library, and to know which compounds have, and have not, been assayed, or to select a representative sample of a library for assay. In an assay with many positive interactions, (e.g., a focussed library designed to optimize a previous positive interaction), it is possible to quantitate relationships between structure and activity among the positively identified compounds. Furthermore, the process of identifying each compound takes place only once. Therefore, if multiple screens are desired, throughput is much faster since there is no need to decode the tag information after each separate assay. It is for these reasons that the pharmaceutical industry is reluctant to replace conventional spatial encoding with the potentially more powerful chemical encoding, and thus has largely failed to take advantage of the efficiency of split and pool chemical synthesis. The current method combines the power of split and pool synthesis with the convenience of spatial encoding.

The encoding of the chemical library with specific tags can be carried out by any of the variety of methods described above. Preferably, the tags are attached to the beads with the same chemistry as the compounds. A discussion of available linkers to attach tags and compounds to the bead is included above. Once the library has been synthesized and encoded, in preferred embodiments, the first step of spatially encoding the library is to array the beads, or other support onto which the compounds and tags have been attached, onto microtiter plates by placing one bead in each well. The placement of beads carrying the library molecules in the microtiter dishes is random. Each compound is then released into the well by any of a variety of release chemistries, forming a stock solution. The tags are also released into the stock solution using the same release chemistry. The resulting mixture of tags and library compounds can then be used both to assay the compounds and identify the tags, as described below.

Each tag is attached both to a linker and to a chemical "handle" that is designed to allow capture of the tag on derivatized glass. For example, the glass may be derivatized with either thiol or maleimide groups that will covalently capture the tag molecules via a thiol group on the tag molecule. Methods of attaching various chemical groups to tag molecules and glass surfaces are well known to those skilled in the art. Indeed, any chemical interaction that attaches the tag molecule to the glass slide would be within the scope of this aspect of the present invention.

Creation of the spatial array involves transfer of very small volumes of the stock solutions (containing the released tags) onto the chemically modified glass slide. One currently available arraying technology that is amenable to analysis of tag molecules is the technology used to print DNA sequences onto glass slides to produce the "DNA chips" used in the analysis of relative mRNA expression levels (DeRisi et al., *Science*, October 24;278(5338):680–6, 1997). Using this DNA printer, 10,000 spots corresponding to six 1,536 well stock plates can be arrayed on one slide in an area 25 millimeters square. One of ordinary skill in the art will recognize that any mechanism capable of recreating a similar array of droplets can be used in the present invention. One particular advantage of this aspect of the invention is that many identical slides can be made simultaneously. Alternatively, many identical slides can be made in rapid succession. Furthermore, multiple non-identical plates can be spotted either simultaneously or sequentially. Additionally, a trivial volume of stock solution will be used for tag identification, allowing for a large number of assays to be conducted on each individual compound in the library.

The result of the above procedure is a spatial array of tags representing a chemical library created preferably by split and pool techniques. The array of spots derived from individual wells of the stock plates contain 1–30 covalently bound tag molecules. Once the spatial array has been created, the tags representing each compound in the library are decoded. Any of the identification units of the present invention can be used to decode the spatially encoded chemical library. A particularly preferred identification unit for decoding spatially encoded chemical libraries is one that includes a fluorescent signal. In preferred embodiments, the identification unit is a specific small molecule tag that is recognized by a fluorescently labeled antibody binding partner. At least three fluorescent color channels can be distinguished in analysis. Therefore, it is possible to decode 30 tags from one specific bead by using 10 identically printed slides per library. For example, binding partners 1, 2, and 3 will be labeled by color 1, 2, and 3 respectively and used on slide one. Next, binding partners 4, 5, and 6 will be labeled by colors 1, 2, and 3 respectively and used on slide 2, and so forth. Imaging the fluorescent signal emitted by the tag can be performed using for example, an Arrayworks imager (Applied Precision). Using this instrumentation, the number of molecules present per spot would be at least 1000 times the number required for imaging.

According to the technology of the present invention, all of the information about the tags present on every bead in a spit and pool library can be captured in a stack of thirty hapten images, allowing the immediate identification of compounds that exhibit positive interactions in a particular assay. Additionally, information can be gathered regarding the identity of compounds that do not exhibit positive interactions or exhibit only weak interactions when assayed. Furthermore, compounds can be assessed for other effects, for example, non-specific cytotoxicity. Utilization of this wealth of information in an efficient way can be facilitated by the employment of bioinformatics. The similarity in the information obtained from SESPLs can be managed by approaches already developed for conventional spatially encoded libraries.

In yet another preferred embodiment of the present invention, the beads themselves can be spatially arrayed. A system that arrays the solid supports, preferably beads, containing the attached tags onto plates linearly eliminates the step of detaching the tag from the bead. One method of linearly arraying the beads is to place the beads in capillary tubes with a diameter only slightly larger than the bead so that the beads are held in a line inside of the capillary tube. For example, beads 20–90 micrometers in diameter can be used to fill capillary tubes approximately 110 micrometers in diameter. The limited diameter of the capillary tube holds the beads in a linear array and prevents the beads from forming a group (e.g., 100 beads per row). A fluid handling system is used to pass fluid containing the binding partner past the beads without moving the beads out of the linear array. Using this technique, an image may be taken of 100 rows of capillaries at one time, or 10,000 beads.

Another preferred method of spatially arraying the beads is to use a plate with a linear array of indentations. For example, beads may be loaded onto a glass plate containing a linear array of indentations and the beads allowed to settle into the indentations. Another plate may be placed on top of the first plate to hold the beads in place. This second plate may be indented to match the indentations on the first plate or not indented. Fluid containing the binding partners are then allowed to circulate throughout the plate and flow past the beads for recognition and binding of the tags. This method of spatially arraying the beads is particularly preferred because a plate with a linear array of indentations has a higher capacity for beads than does the capillary tube system. Using the indented plates approximately 10,000 beads can be imaged simultaneously.

The binding partners used to detect the tags on the spatially arrayed beads may be macromolecules capable of specific and tight binding to a small molecule hapten, including nucleic acids and proteins. Preferably, the binding partners are oligonucleotides, particularly derivatized oligonucleotides. More preferably, the binding partners are nucleic acids, particularly single stranded RNA molecules. Most preferably, the binding partner is a protein, particularly an antibody. Particularly preferred labels for identifying the tags by imaging signals emitted by the beads on the plate include luminescent and fluorescent labels.

Thus, the present invention further provides methods for combining the advantages of split and pool synthesis with the convenience of spatial encoding by creating retrospectively spatially encoded split and pool libraries. Those of skill in the art will recognize that any type of library can by spatially encoded using the methods of the present invention.

One of ordinary skill in the art will further realize that the present invention is not limited to applications involving decoding chemical structures, but rather may be employed in many contexts and disciplines. Specifically, the inventive identification system may be used to identify any item of interest that is or has been associated with a solid support, whether or not the item is a chemical compound.

EXAMPLES

The present invention can be further understood through consideration of the following on-limiting Examples.

Example 1

Detection

One aspect of the present invention is to tag TANTAGEL beads containing chemical libraries with haptens and recognize them with antibodies. We have developed a model hapten-antibody system, specifically, commercially available digoxigenin (dig) and a mouse antibody to this hapten (anti-dig), (Boehringer Manheim).

Ninety (90) micrometer TANTAGEL-amine beads were mixed with dig-NHS ester at different concentrations to covalently label the beads with dig. Dig-NHS was added in amounts sufficient to label 100%, 10%, 1%, 0.1%, 0.01% and 0.001% of the amino groups. The remaining amino groups were capped with acetic anhydride, and the beads were washed.

Dig-labeled beads were incubated with anti-dig (1 microgram/ml) in the presence of BSA and buffer. The beads were washed, incubated with alkaline phosphatase (AP)-coupled goat anti-mouse antibody, and washed again. Then a chromogenic precipitating substrate (commercially available) for detecting AP was added. Blue color on the beads indicates the presence of AP, and thus effective detection of the dig hapten by antibody.

FIG. 1 shows beads coupled with 0. 1%, 0.01%, and 0.001% dig. The blue color is bright down to 0.1%, and clearly visible at 0.01%. Below this level the staining was the same as unlabeled beads. Other small molecules on the beads such as pyrene and the Wang linker at 100% coupling gave no staining indicating that recognition of the hapten by antibody is specific. This detection method shows that antibody recognition of the hapten on beads works and is highly sensitive. For comparison, the Still method of off bead tagging with GC detection requires coupling of tag molecules at the level of 2% of bead chemistry with 90 micron beads for reliable detection. With AP detection the hapten-antibody method is 100× more sensitive, and we anticipate that the PCR should allow even greater sensitivity.

Example 2

Tag Synthesis

We will develop 20–30 haptens that are recognized by cognate antibodies and can be used to encode/decode the structures of chemical compounds within a library. Several design considerations are important:

i) The haptens must be immunogenic;

ii) The antibodies must not cross react between haptens;

iii) The antibodies must not recognize diverse library molecules; and iv) The haptens must resist chemical reaction conditions and reagents used during library synthesis.

Many chemical solutions can be found to these problems.

We are synthesizing two sets of structures. First a set of bi-aryl amides with an amino hexanoyl spacer for matrix attachment will be synthesized. These are made on a solid phase resin (Wang resin) by acylating amino hexanoic acid with a carboxy, arnino-substituted aromatic group, and acylating the resulting aromatic amine with an aromatic acyl chloride followed by cleavage and purification. Several tags have been made and characterized.

Second a set of aminocapped peptides will be synthesized. These are made by standard solid phase synthesis. These tags incorporate charged functionality (ie., —COOH groups) that will facilitate antibody recognition. The antibodies will be raised to the deprotected form of the tags. When used for tagging, the peptides will be coupled to TANTAGEL(or similar resin) in a protected form. The protecting group used will be an acid-labile tBu ester. The tBu groups will protect the tags during library synthesis. Following library synthesis and assay, when it is necessary to decode the tags by antibody recognition, the beads will be treated with TFA to deprotect the tags and allow antibody binding. Thus each tag will be synthesized in two forms, with protecting groups for tag attachment (e.g., Gly-Ahx-Asp(tBu)-TFMBZ), and without (e.g., Cys-Ahx-Asp-Asp-TFMBZ) protecting groups for immunization and antibody purification. The protected tags for resin coupling have a terminal COOH group. The unprotected tags for protein coupling and immunization have a cys residue for thiol chemistry coupling. All the tags shown in FIG. 2 have been made and characterized.

A major design consideration will be to solve problem iii) above. Although each tag is chemically distinct, different tags contain common chemical substructures. During antibody purification and characterization we will remove any antibodies that cross react between tags. The antibodies we are generating will thus see the whole tag, not a substructure. Such antibodies will not recognize functionality that may be present on library molecules.

Example 3

Antibody Synthesis

The haptens shown, and similar new ones, will be used to immunize rabbits. Specific polyclonal antibodies will be purified from sera by positive affinity purification on cognate hapten, and negative adsorption on a mixture of all the non-cognate tags. A set of double stranded oligonucleotides with common 5' and 3' sequences, that differ in length and/or internal sequence will be prepared. Each different oligonucleotide will be coupled to a distinct antibody. We will use either biotin-streptavidin chemistry of thiol-maleimide coupling with appropriately 5'-modified oligos for this. We will investigate different chemistries for coupling haptens to beads after each step of library synthesis. These will include simple acylation chemistry, and carbene insertion chemistry. We will develop PCR and fluorescence sequencing methods for rapid analysis of which oligos are present in a mixture-first in solution, then for oligos bound to beads via antibody-hapten interactions.

Example 4

Fluorescent Detection of a Binding Partner/Tag Interaction

Coupling of Fluorescent Labels to Antibodies:

Both fluorescein and rhodamine isothiocyanate derivatives are available for coupling reactions. (See Harlow and Lane, pp. 354–355, supra; Fitzwater et al., *Meth. Enz.*, 1996, 267, 275–301, incorporated by reference herein)

Detection Using a Primary Antibody:

We plan to detect a binding partner/tag interaction on a solid support, for example, a TENTAGEL bead. First, the beads will be assayed by any of a variety of mechanisms to identify beads of interest (e.g., beads that have chemical compounds attached that react with a substrate of interest). Second, the background level of fluorescence will be collected from the bead of interest that has not been exposed to the antibody binding partner. Next, the bead will be exposed to the antibody binding partner that has been labeled with a fluorescent tag and specifically recognizes and binds to one of the tags on the bead (Harlow and Lane, supra). The beads will be washed with a denaturant solution that will remove non-specific binding of the antibody to the bead. The new fluorescent signal will be collected using fluorescent imaging quantitation. This process will then be repeated using an antibody binding partner specific to a different tag. Any number of tags on a bead may be identified using this technique.

Detection Using a Secondary Antibody:

As described above, a binding partner/tag interaction will be detected while attached to a solid support, for example, a TENTAGEL bead using fluorescence. First, the beads will be assayed by any of a variety of mechanisms to identify beads of interest (i.e., that have chemical compounds attached that react with a substrate of interest). Second, the background level of fluorescence will be collected from the bead of interest that has not been exposed to the antibody binding partner. Next, the bead will be exposed to the antibody binding partner that specifically recognizes one of the tags but has not been fluorescently labeled (Harlow and Lane, supra). The beads will be washed with a denaturant solution to remove non-specific binding of the antibody to the tag. A second antibody, or "secondary antibody", that specifically recognizes and binds to the first antibody will be exposed to the tag/binding partner complex that has previously formed on the bead. The secondary antibody is allowed to bind to the primary antibody binding partner already bound to the tag on the bead, and the beads are washed with a denaturant solution that will remove non-specific binding of the secondary antibody to the bead. The new fluorescent signal emitted by the label on the secondary antibody will be collected using fluorescent imaging quantitation. This process will then be repeated using a antibody binding partner specific to a different tag. As mentioned above, any number of different binding partner/tag interactions may be detected on a single bead.

Example 5

Use of Nucleic Acid Labels

Biotin Labeling of Antibodies:

Most biotinylations are preformed using a succinimide ester of biotin. The coupling is done through free amino groups on the antibody or other protein, normally lysyl residues. Harlow and Lane, p. 341, supra, incorporated herein by reference).

Detection of the Nucleic Acid:

A bead containing a compound of interest will be incubated with a panel of antibodies, each of which binds specifically to a particular tag that might be on the bead, and each of which is associated with a particular DNA label. The antibody binding partners will be allowed to bind to the tags. After binding, the beads will be washed with a stringent solution to remove the antibodies that bind non-specifically to the surface of the bead (See Harlow and Lane, supra). The DNA labels, coupled to the binding partner, will be detected by amplification, on or off the solid support, by using the PCR (see McPherson, supra). For RNA labels, a prior step of reverse transcription will be carried out. The oligonucleotide primers used for amplification will be approximately 20 nucleotides in length and correspond to common sequences located at the ends of the DNA label. The amplification reaction will contain all of the ingredients required for a PCR reaction, except all deoxyribonucleotides, (e.g., adenine, thymine, and cytosine) excluding guanine, will be added to the reaction. The first guanine nucleotide of the DNA label will be placed at a unique position relative to other labels representing different identification units. The polymerization will not proceed past the first guanine nucleotide because the PCR reaction mixture lacks a guanine to place in that position. The resulting PCR products will be applied to a sequencing gel (see Ausubel et al., supra) to identify the length of the DNA label, thereby revealing the identity of the chemical compound the identification unit represents.

Example 6

Nucleic Acids as Binding Partners

We plan to develop single stranded nucleic acids (RNA or DNA aptamers) for recognition of the tag directly. We will start with two RNA aptamers that recognize theophylline, and ATP or AMP, respectively (Jenison et al., *Science*, 163, 1425–1429; Sassanfar et al., *Nature*, 1993, 364, 550–553). We will make these RNA aptamers and allow them to couple to the two model tags attached to the TENTAGEL at different levels. We will then test the sensitivity and specificity by which the aptamers can recognize their ligands and thus decode the beads. For detection we will use the PCR with a prior reverse transcription step for RNA. If this is successful, we will proceed to making RNA or DNA aptamers to our hapten tags by synthesis of random sequences, and cycles of affinity enrichment and amplification using SELEX-type procedures (Klugh et al., *Mol. Biol. Reports*, 1994, 20, 97–107). We may need to synthesize new structures, e.g. using (protected) Arg and Lys in place of Asp and Glu on the peptide tags (see FIG. 4).

For aptamers, no antibody coupling step is needed. For tag readout, we will simply incubate multiply tagged beads with the aptamer mixture, wash the beads, co-amplify the bound aptamers using the PCR, and detect which sequences are present or absent by one of the PCR- or sequence-based methods described above.

Example 7

Hapten Tag Synthesis and Antibody Specificity

The chemical structures of fourteen hapten tags which were synthesized and worked well in the instant invention are shown in FIG. 5. These tags are based on bi-aryl amides with an amino hexanoyl spacer for attachment to the matrix. Out of 18 potential hapten tags which were designed, 14 of these worked well in terms of being able to develop polyclonal antibodies specific for each hapten structure.

These haptens were used to immunize rabbits and specific polyclonal antibodies were purified as described above in Example 2. ELISA data demonstrating the specificity of the developed polyclonal antibodies is shown below in the table. The columns represent the hapten tags on the ELISA plate, and the rows represent the antibodies used to probe the plate. The numerical value listed is the signal minus background. A standard ELISA protocol was used with alkaline phosphatase detection.

Antibody/Hapten Specificity

|   | Hap-A | Hap-E | Hap-F | Hap-G | Hap-H | Hap-I | Hap-J | Hap-K | Hap-L | Hap-N | Hap-R | Hap-T | Hap-U | Hap-V |
|---|---|---|---|---|---|---|---|---|---|---|---|---|---|---|
| A | 2.085 | 0.000 | 0.001 | −0.002 | 0.003 | 0.005 | 0.136 | 0.020 | 0.017 | −0.004 | 0.245 | −0.001 | −0.004 | 0.012 |
| E | 0.000 | 1.129 | 0.006 | 0.000 | 0.004 | 0.003 | −0.005 | 0.012 | 0.015 | 0.017 | −0.006 | 0.066 | −0.001 | −0.002 |
| F | 0.000 | 0.007 | 1.650 | 0.002 | 0.110 | 0.001 | −0.007 | 0.003 | 0.017 | 0.003 | −0.004 | −0.003 | −0.004 | −0.003 |
| G | 0.003 | −0.002 | 0.007 | 1.681 | 0.006 | 0.000 | 0.002 | 0.008 | 0.018 | −0.006 | −0.004 | 0.003 | 0.009 | 0.012 |
| H | 0.000 | −0.002 | 0.002 | 0.001 | 1.100 | 0.005 | −0.001 | 0.001 | 0.008 | 0.000 | 0.002 | −0.003 | −0.001 | −0.004 |
| I | 0.009 | −0.003 | 0.005 | 0.007 | 0.066 | 1.945 | 0.023 | 0.358 | 0.018 | 0.005 | 0.002 | −0.004 | −0.002 | −0.003 |
| J | 0.279 | 0.000 | −0.004 | 0.002 | −0.002 | −0.001 | 2.007 | 0.003 | 0.001 | 0.000 | 0.015 | 0.000 | 0.000 | −0.002 |

-continued

|   | Hap-A | Hap-E | Hap-F | Hap-G | Hap-H | Hap-I | Hap-J | Hap-K | Hap-L | Hap-N | Hap-R | Hap-T | Hap-U | Hap-V |
|---|---|---|---|---|---|---|---|---|---|---|---|---|---|---|
| K | 0.059 | 0.002 | −0.003 | −0.003 | 0.087 | 0.150 | −0.004 | 1.265 | −0.013 | −0.002 | 0.000 | 0.001 | −0.002 | 0.003 |
| L | −0.008 | −0.007 | 0.357 | 0.017 | 0.021 | −0.006 | −0.005 | −0.003 | 1.569 | 0.053 | −0.001 | −0.004 | −0.002 | 0.000 |
| N | 0.006 | −0.012 | 0.001 | −0.003 | −0.009 | 0.003 | −0.004 | −0.005 | 0.090 | 1.237 | −0.003 | −0.003 | −0.002 | −0.002 |
| R | 0.155 | −0.007 | −0.008 | −0.007 | 0.001 | −0.006 | 0.010 | 0.011 | 0.000 | −0.005 | 1.395 | −0.004 | −0.002 | 0.017 |
| T | −0.005 | 0.000 | −0.004 | 0.003 | 0.000 | −0.002 | −0.001 | 0.001 | 0.000 | 0.001 | −0.001 | 1.354 | −0.003 | 0.316 |
| U | −0.010 | −0.001 | 0.004 | 0.004 | −0.001 | 0.000 | 0.005 | −0.004 | 0.001 | 0.004 | 0.001 | 0.022 | 0.865 | 0.021 |
| V | −0.008 | 0.002 | 0.002 | 0.003 | 0.002 | 0.001 | 0.000 | 0.001 | 0.005 | 0.004 | −0.004 | 0.094 | 0.100 | 1.050 |

All the numbers on the diagonal which represent cognate recognition are high, while the numbers off the diagonal are low. Using a cutoff of 0.5 units or greater, all the cognates are positive, and all the non-cognates are negative.

Example 8

Attaching Tags and Library Molecules to Beads

Figure 6:
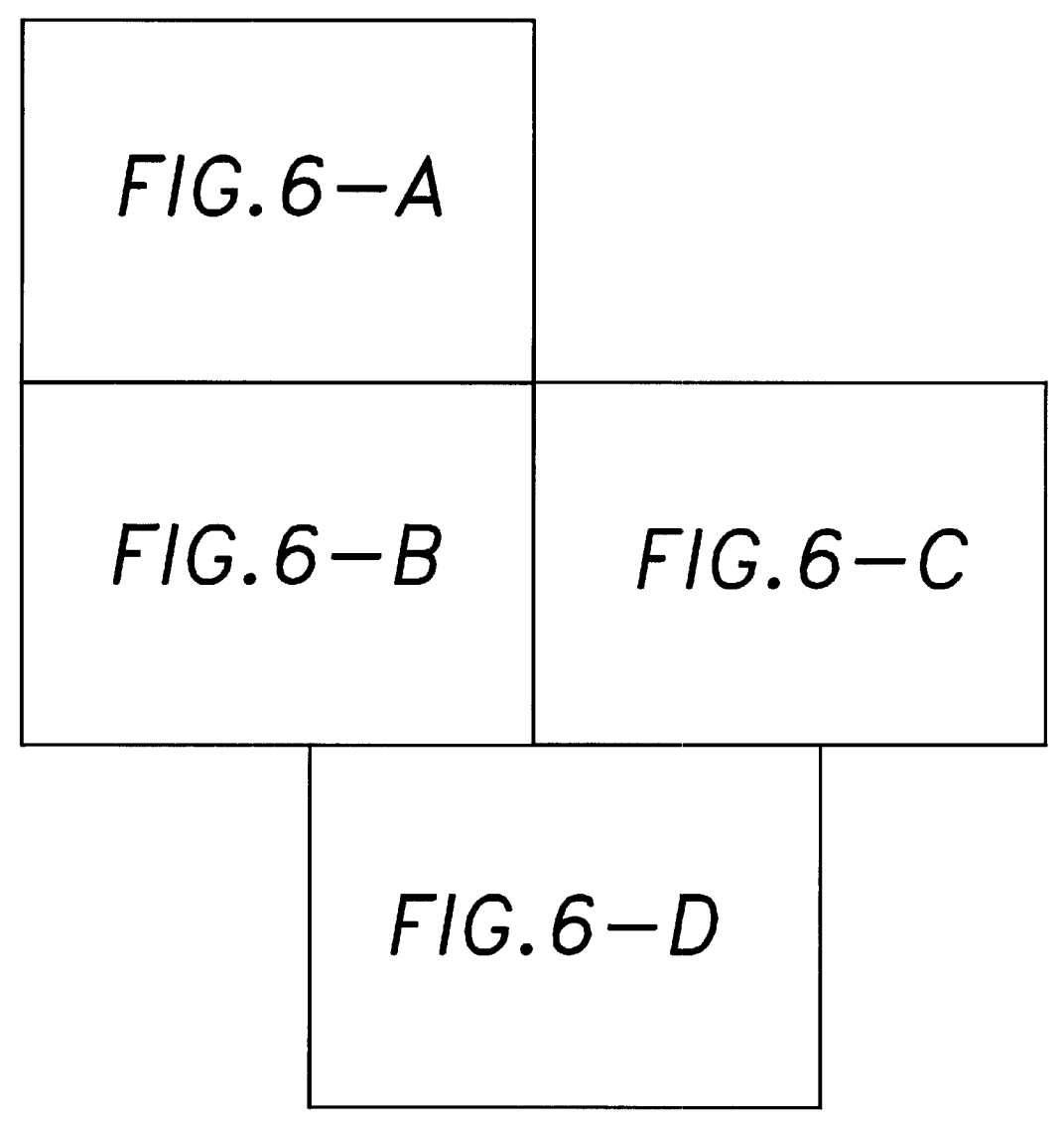

In the scheme shown in FIG. 6, both tags and library molecules were attached to a polystyrene bead. Tags were attached on the outside of the bead, and library molecules were placed on the inside. The scheme begins with a 500 micron polystyrene bead with free amino groups inside and outside the bead. The free amine groups on the outside were first reacted with an Fmoc-NH-PEG-CO-NHS activated ester which selectively protects the outside amino sites with an Fmoc group due to its bulkiness. The inside amino groups are then used in attaching/synthesizing the library molecules. After the synthesis of the library molecule is complete, the Fmoc groups are removed, and the hapten tag is added to the free amino groups on the outside of the bead. Orthogonal protecting groups were used in the synthesis of the library molecules and the hapten tag.

This scheme was executed for several library molecules and four tags. The synthesis of library molecules was confirmed by LC-MS analysis, and the presence of the tag was confirmed by ELISA using antibodies and alkaline phosphatase development.

Example 9

Multiple Chemical Transformations of a Library Molecule on a Bead with an Attached Tag In the scheme shown in FIG. 7, again both tags and library molecules were attached to a polystyrene bead. The free amino groups on the outside of the bead were selectively modified with Fmoc-NH-PEG-CO-NHS. The remaining free amino groups on the inside of the bead were coupled to Boc-Ala-OH. The Fmoc protecting groups on the outside was removed, and the hapten tag was coupled onto the free outside amino group. The library molecule was then synthesized on the inside of the bead using four chemical transformations.

Figure 7:
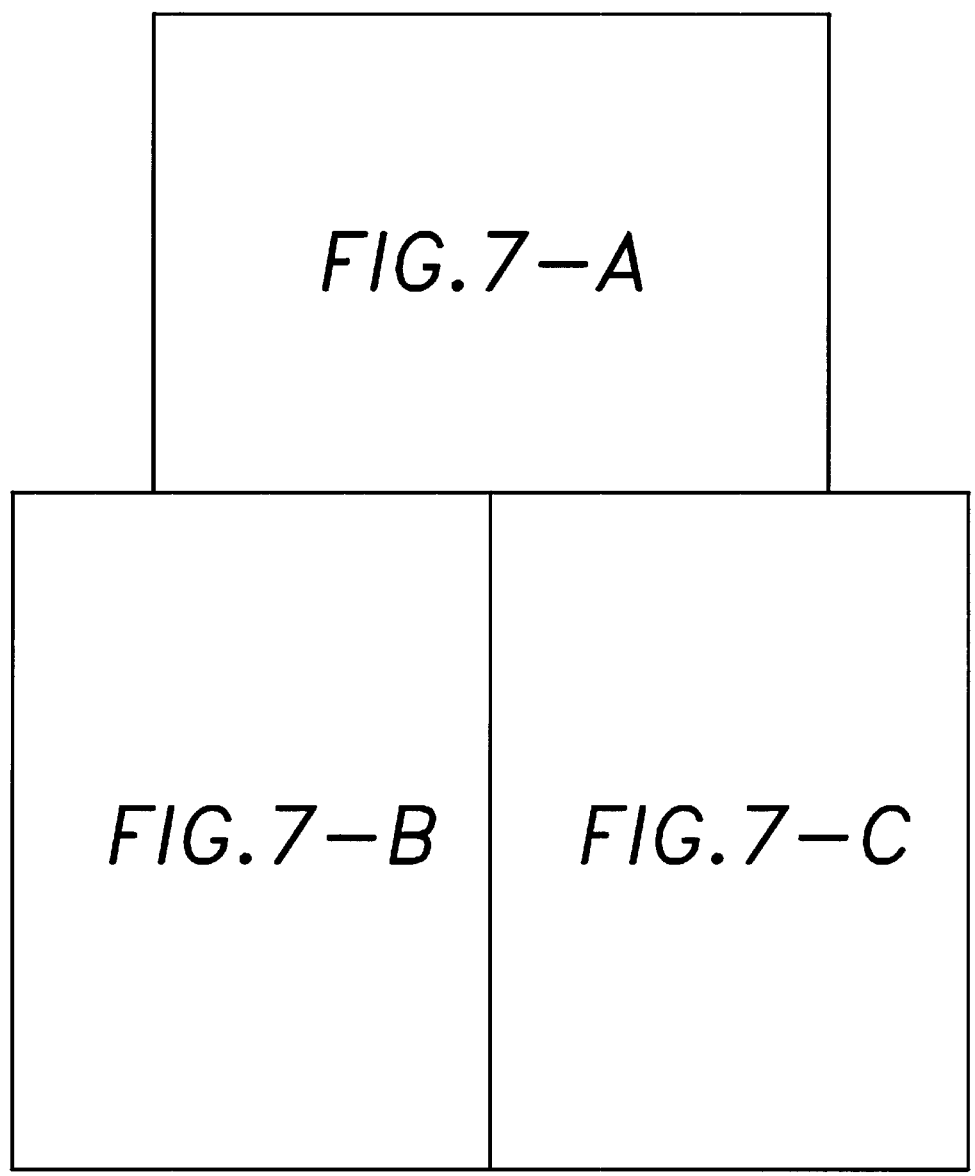
FIG. 7. A scheme showing the synthesis of the hapten tag on the outside of the bead and the library of compounds on the inside of the bead. Graph shows antibody detection of a single bead after each step of the library synthesis.

The bead was probed after each of the four transformations as shown in the graph in FIG. 7. The signal from the tag was undiminished indicating that the tags can be detected after synthesis of the library molecules. The signals shown in the graph were recorded from a single bead.

Example 10

Sequential Detection of Two Tags on One Bead

Four beads were prepared to allow for sequential detection of two tags on one bead since multiple tags on one bead will need to be detected in order to discern the reaction history of a bead during the synthesis of a full library.

The beads were 500 micron polystyrene beads with a model library molecule (quinaldic acid) attached to internal sites and with a PEG spacer and hapten attached to external sites. One bead was prepared with hapten A alone, one with hapten E alone, one with both haptens A and E, and one with no hapten (control).

The beads were first incubated with anti-A antibody, and the signal was developed with alkaline phosphatase. The beads were then stripped with 0.2 N NaOH for 30 minutes to remove any anti-A antibody. Beads were then incubated with anti-E antibody, and the signal was developed with alkaline phosphatase. Results with the background from the control bead subtracted out are shown below:

|   | A-Beads | E-Beads | A,E-Beads |
|---|---|---|---|
| Probe with anti-A Ab | 0.255 | 0.123 | 0.225 |
| Probe with anti-E Ab | 0.152 | 0.33 | 0.341 |

By setting the threshold for a positive signal at 0.2 and above, the beads were correctly decoded.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A method of decoding a chemical library by determining structural or synthetic features of compounds in the chemical library, the method comprising steps of:
   providing a plurality of solid supports, each of which comprises:
     an attached chemical compound whose structure is to be determined; and
     a tag selected to represent a structural or synthetic feature of the chemical compound, wherein the tag is present on the solid support at less than or equal to $10^{-12}$ moles on each support;
   detaching the tags from the solid supports; and
   identifying the tags by a method comprising steps of:
     providing a plurality of binding partners, each of which binds specifically and detectably to at least one tag;
     contacting the released tags with the plurality of binding partners; and
   detecting binding of at least one binding partner to at least one tag, the existence of such binding indicating the bound tag was present on the solid support, which presence in turn indicates that the structural or synthetic feature represented by the tag was present in the chemical compound.

2. The method of claim 1, the method further comprising step of:

distributing the solid supports onto a microtiter plate prior to detaching the tags.

3. The method of claim 2 wherein in the step of distributing, the solid supports are distributed onto the microtiter plate at one solid support per well.

4. The method of claim 2 wherein, the step of detaching further comprises releasing the tags into wells of the microtiter plate containing a liquid.

5. The method of claim 4 wherein, the tags are released by a chemical reaction.

6. The method of claim 4 wherein, the step of detaching further comprises spotting a sample of the liquid from the wells of the microtiter plate onto a slide and attaching the tags to the slide.

7. The method of claim 6 wherein, the step of attaching comprises attaching the tag to the slide through a unique chemical handle.

8. The method of claim 7 wherein, the unique chemical handle comprises:

derivatizing the slide with a thiol group; and derivatizing the tag with a thiol group.

9. The method of claim 6, wherein in the step of spotting, at least 10,000 spots are placed in an area of 25 millimeters.

10. The method of claim 6, wherein in the step of spotting, multiple plates are spotted in sequence.

11. The method of claim 6, wherein in the step of spotting, multiple plates are spotted simultaneously.

12. The method of claim 1 wherein, the step of identifying comprises detecting a fluorescent signal.

13. The method of claim 1 wherein, the step of identifying comprises detecting a luminescent signal.

14. A method of decoding a chemical library by determining structural or synthetic features of compounds in the chemical library, the method comprising steps of:

providing a plurality of solid supports, each of which comprises:

an attached chemical compound whose structure is to be determined; and a tag selected to represent a structural or synthetic feature of the chemical compound, wherein the tag is present on the solid support at less than or equal to $10^{-12}$ moles on each support; and identifying the tags by a method comprising steps of:

providing a plurality of binding partners, each of which binds specifically and detectably to at least one tag;

contacting the plurality of solid supports with the plurality of binding partners; and detecting binding of at least one binding partner to at least one tag, the existence of such binding indicating the bound tag was present on the solid support, which presence in turn indicates that the structural or synthetic feature represented by the tag was present in the chemical compound.

15. The method of claim 14, the method further comprising step of:

spatially arraying the solid supports in a capillary tube.

16. The method of claim 15 wherein, the diameter of the capillary tube is slightly larger than the solid support so the solid supports are held in a linear array.

17. The method of claim 15 wherein, fluid is circulated through capillary tubes containing solid supports.

18. The method of claim 14, the method further comprising step of:

spatially arraying the solid supports on a first plate with linear indentations that hold the solid supports in a linear array.

19. The method of claim 18 wherein, the step of spatially arraying the solid supports comprises placing a second plate on top of the first plate to hold the solid supports in the indentations on the first plate.

20. The method of claim 19 wherein, the second plate is also indented.

21. The method of claim 19 wherein, the second plate is not indented.

22. The method of claim 18 wherein, the plates are glass.

23. The method of claim 14 wherein, the step of providing a plurality of binding partners comprises circulating fluid containing the binding partners past the solid supports.

24. The method of claim 18 wherein, fluid is circulated throughout the indents of an indented plate containing solid supports.

25. The method of claim 14 wherein, in the step of providing a plurality of binding partners, the binding partner provided is an antibody binding partner.

26. The method of claim 25 wherein, the binding partner is labeled with a fluorescent label.

27. The method of claim 25 wherein, the binding partner is labeled with a luminescent label.

28. The method of claim 14 wherein, the step of identifying comprises detecting a fluorescent signal.

29. The method of claim 14 wherein, the step of identifying comprises detecting a luminescent signal.

* * * * *

UNITED STATES PATENT AND TRADEMARK OFFICE
CERTIFICATE OF CORRECTION

PATENT NO. : 6,541,203 B2  Page 1 of 1
APPLICATION NO. : 09/448395
DATED : April 1, 2003
INVENTOR(S) : Timothy J. Mitchison It is certified that error appears in the above-identified patent and that said Letters Patent is hereby corrected as shown below:

In column 1, beginning at line 12 and ending at line 14, under the subtitle "Government Support," please delete:

"The work described herein was supported by National Cancer Institute grant number CA78048. The United States may have certain rights in this invention."

and insert:

--This invention was made with government support under CA78048 awarded by the National Institutes of Health. The government has certain rights in this invention.--

Signed and Sealed this

Twentieth Day of January, 2009

JON W. DUDAS
*Director of the United States Patent and Trademark Office*